US010864276B2

(12) United States Patent
Harris et al.

(10) Patent No.: US 10,864,276 B2
(45) Date of Patent: Dec. 15, 2020

(54) ACTIVATED POLYOXAZOLINES AND CONJUGATES AND COMPOSITIONS COMPRISING THE SAME

(71) Applicant: Serina Therapeutics, Inc., Huntsville, AL (US)

(72) Inventors: J Milton Harris, Huntsville, AL (US); Kunsang Yoon, Madison, AL (US); Michael David Bentley, Huntsville, AL (US); Zhihao Fang, Madison, AL (US); Tacey Viegas, Madison, AL (US); Francesco Maria Veronese, Padua (IT); Anna Mero, Padua (IT)

(73) Assignee: Serina Therapeutics, Inc., Huntsville, AL (US)

( * ) Notice: Subject to any disclaimer, the term of this patent is extended or adjusted under 35 U.S.C. 154(b) by 0 days.

(21) Appl. No.: 16/144,358

(22) Filed: Sep. 27, 2018

(65) Prior Publication Data

US 2019/0070301 A1  Mar. 7, 2019

Related U.S. Application Data

(63) Continuation of application No. 15/453,686, filed on Mar. 8, 2017, now Pat. No. 10,086,084, which is a continuation of application No. 14/663,863, filed on Mar. 20, 2015, now abandoned, which is a continuation of application No. 13/961,576, filed on Aug. 7, 2013, now abandoned, which is a continuation of application No. 13/676,048, filed on Nov. 13, 2012, now abandoned, which is a continuation of application No. 13/276,910, filed on Oct. 19, 2011, now abandoned, which is a continuation of application No. 12/622,264, filed on Nov. 19, 2009, now abandoned, which is a continuation-in-part of application No. 12/529,001, filed as application No. PCT/US2008/002626 on Feb. 28, 2008, now Pat. No. 7,943,141.

(60) Provisional application No. 61/116,246, filed on Nov. 19, 2008, provisional application No. 61/116,252, filed on Nov. 19, 2008, provisional application No. 60/892,212, filed on Feb. 28, 2007.

(51) Int. Cl.
| | |
|---|---|
| A61K 47/59 | (2017.01) |
| C07K 7/08 | (2006.01) |
| C07K 14/47 | (2006.01) |
| C07K 14/505 | (2006.01) |
| C07K 14/535 | (2006.01) |
| C07K 14/62 | (2006.01) |
| C12N 9/96 | (2006.01) |
| A61K 31/727 | (2006.01) |
| A61K 31/728 | (2006.01) |
| A61K 38/10 | (2006.01) |
| A61K 38/17 | (2006.01) |
| A61K 38/18 | (2006.01) |
| A61K 38/19 | (2006.01) |
| A61K 38/47 | (2006.01) |
| C08G 69/48 | (2006.01) |
| A61K 38/27 | (2006.01) |
| A61K 38/33 | (2006.01) |
| A61K 38/42 | (2006.01) |

(52) U.S. Cl.
CPC ............ *A61K 47/59* (2017.08); *A61K 31/727* (2013.01); *A61K 31/728* (2013.01); *A61K 38/10* (2013.01); *A61K 38/1719* (2013.01); *A61K 38/1816* (2013.01); *A61K 38/193* (2013.01); *A61K 38/27* (2013.01); *A61K 38/33* (2013.01); *A61K 38/42* (2013.01); *A61K 38/47* (2013.01); *C07K 7/08* (2013.01); *C07K 14/47* (2013.01); *C07K 14/505* (2013.01); *C07K 14/535* (2013.01); *C07K 14/62* (2013.01); *C08G 69/48* (2013.01); *C12N 9/96* (2013.01); *C12Y 302/01017* (2013.01)

(58) Field of Classification Search
CPC .............. A61K 47/48207; A61K 38/33; A61K 38/193; A61K 38/27; A61K 38/42; A61K 38/1816; A61K 38/47; A61K 31/727; A61K 31/728; C12Y 302/01017; C08G 69/48

See application file for complete search history.

(56) References Cited

U.S. PATENT DOCUMENTS

| | | |
|---|---|---|
| 5,672,662 A | 9/1997 | Harris |
| 6,890,518 B2 | 5/2005 | Patton |

(Continued)

FOREIGN PATENT DOCUMENTS

| | | |
|---|---|---|
| WO | 03066069 | 8/2003 |

OTHER PUBLICATIONS

Greene, T., et al.; Protective Groups in Organic Synthesis, 3rd Edition, 1999, p. 369-453.*

(Continued)

*Primary Examiner* — Robert S Jones, Jr.
(74) *Attorney, Agent, or Firm* — Thomas G. Peterson; Maynard Cooper & Gale

(57) ABSTRACT

The present disclosure provides POZ derivatives having a range of active functional groups allowing conjugation of POZ derivatives to a variety of target molecules under a wide range of reaction conditions to produce a hydrolytically stable target molecule-POZ conjugate. Furthermore, the present disclosure provides novel methods of synthesis for the disclosed POZ derivatives and hydrolytically stable target molecule-POZ conjugates created using the disclosed terminally activated monofunctional POZ derivatives. In one embodiment, the POZ derivative is a terminally activated monofunctional POZ derivative.

12 Claims, 8 Drawing Sheets

Specification includes a Sequence Listing.

(56) References Cited

U.S. PATENT DOCUMENTS

| | | |
|---|---|---|
| 7,732,561 B2 | 6/2010 | Kataoka |
| 2004/0266690 A1 | 12/2004 | Pool |
| 2005/0009988 A1* | 1/2005 | Harris .................. C08G 65/329 525/56 |
| 2005/0226843 A1 | 10/2005 | Zhao |
| 2006/0051315 A1 | 3/2006 | Scaria |
| 2006/0105046 A1 | 5/2006 | Bentley |

OTHER PUBLICATIONS

Roberts, M.J., et al., "Chemistry for peptide and protein PEGylation," Advanced Drug Delivery Review, 2002, vol. 54, pp. 459-476.

Hsiue, Ging-H0, et al., "Nonviral Gene Carriers Based on Diblock Copolymers of Poly(2-ethyl-2-oxazoline) and Linear Polyethylenimine," bioconjung Cehm. May-Jun. 206; 17(3); pp. 781-786.

Jordan, Rainer, et. al., Lipopolymers for Surface Functionalizations. 1. Synthesis and Characterization of Terminal Functionalized Poly(N-propionylethylenimine)s; Macromolecules, vol. 34, No. 26, Dec 2001.

Zalipsky, Samuel, et al., "Evaluation of Blood Clearance Rates and Biodistribution of Poly(2-oxazoline)-Grafted Liposomes," Journal of Pharmaceutical Sciences, vol. 85, No. 2, Feb. 1996; pp. 137-137.

Gross, Aurelia, et al., "Synthesis and copolymerization and macromonomers based on 2-nonyl-and 2-phenyl-2-oxazoline," Macromolecular Chem. & Phys. vol. 197; 1996; pp. 2811-2826.

Sato, Haruya, "Enzymatic procedure for site-specific pegylation of proteins," Advanced Drug Delivery Reviews; vol. 54; 2002; pp. 487-504.

Kukolka, Florian, Extended European Search Report (Europe Patent App No. 08726203.6); May 2, 2016.

Nilsson, K., et al., "Immobilization of Ligands with Organic Sufonyl Chlorides," Methods in Enzymology, vol. 104, 1984, pp. 56-69.

Cesana, S., Functionalization of poly(2-oxazoline)s with cyclic RGD peptides, 2004.

Miyamota, Masatoshi, et al., "Preparation and Enzymatic Activity of Poly[(N-acylimino)ethylene]-Modified Catalase," Macromolecules, vol. 23, No. 13, Jun. 25, 1990, pp. 3201-3205.

Spoden, Giles, et al., "Polyethylenimine is a strong Inhibitor of Human Papillomavirus and Cytomegalovirus Infection," Antimicrobial Agents and Chemotherapy, vol. 56, No. 1, Oct. 3, 2011, pp. 75-82.

Guo, Hongyun, et al., "Preparation of Dialkyl Disulfides via Reduction of Alkylthiocyantes with TiCl/SM System," Synthetic Communications, vol. 27, No. 15, 1997; pp. 2721-2724.

* cited by examiner

FIG. 1
Initiation
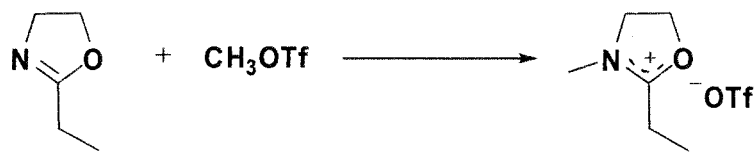
Propagation
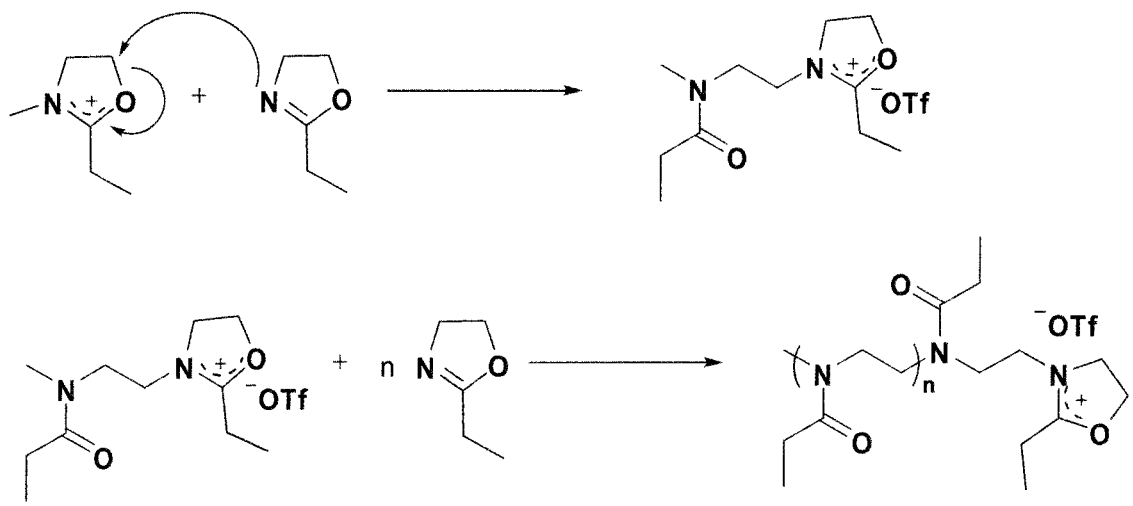
Termination
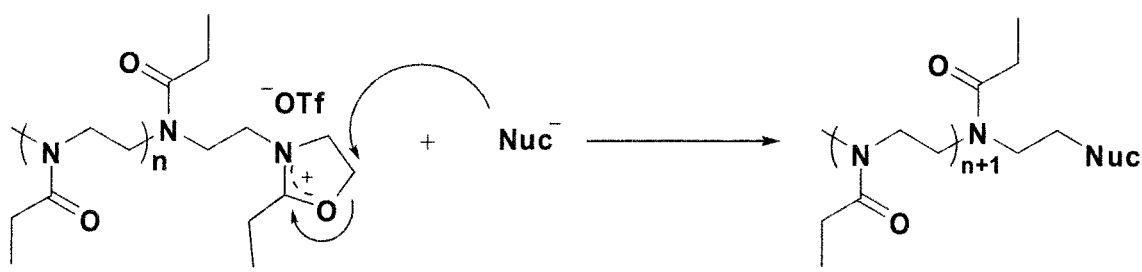

FIG. 3

```
1                                           10                                          20
Ala Pro Pro Arg Leu Ile Cys Asp Ser Arg Val Leu Glu Arg Tyr Leu Leu Glu Ala Lys
Glu Ala Glu Asn Ile Thr Thr Gly Cys Ala Glu His Cys Ser Leu Asn Glu Asn Ile Thr
Val Pro Asp Thr Lys Val Asn Phe Tyr Ala Trp Lys Arg Met Glu Val Gly Gln Gln Ala
Val Glu Val Trp Gln Gly Leu Ala Leu Leu Ser Glu Ala Val Leu Arg Gly Gln Ala Leu
Leu Val Asn Ser Ser Gln Pro Trp Glu Pro Leu Gln Leu His Val Asp Lys Ala Val Ser
101                                         110                                         120
Gly Leu Arg Ser Leu Thr Thr Leu Leu Arg Ala Leu Gly Ala Gln Lys Glu Ala Ile Ser
Pro Pro Asp Ala Ala Ser Ala Ala Pro Leu Arg Thr Ile Thr Ala Asp Thr Phe Arg Lys
Leu Phe Arg Val Tyr Ser Asn Phe Leu Arg Gly Lys Leu Lys Leu Tyr Thr Gly Glu Ala
Cys Arg Thr Gly Asp
                165
```

FIG. 4

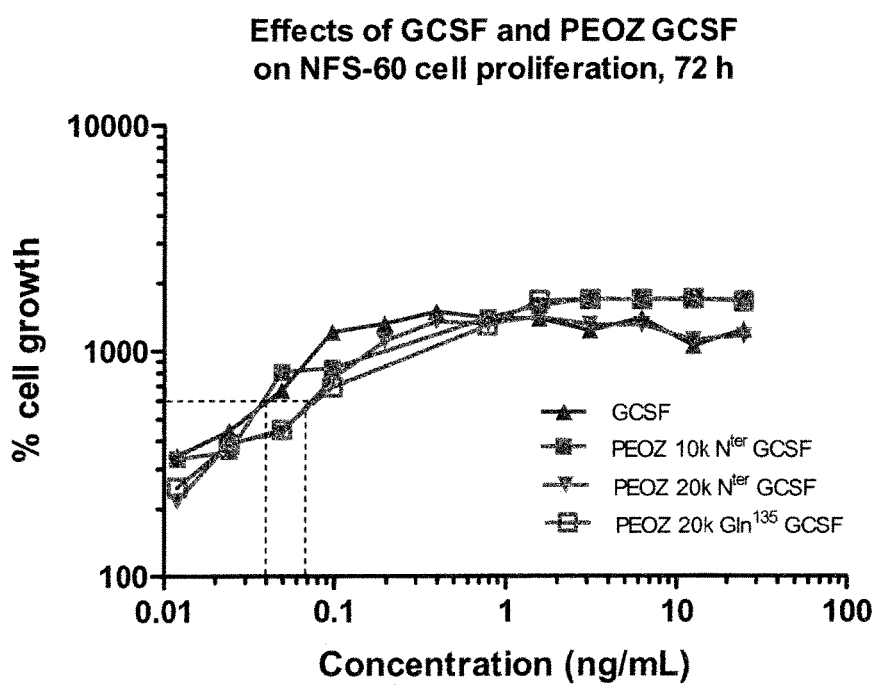

ACTIVATED POLYOXAZOLINES AND CONJUGATES AND COMPOSITIONS COMPRISING THE SAME

CROSS REFERENCE TO RELATED APPLICATIONS

The present application is a continuation of U.S. application Ser. No. 15/453,686, filed Mar. 8, 2017 (currently pending). U.S. application Ser. No. 15/453,686 is a continuation of U.S. application Ser. No. 14/663,863, filed Mar. 20, 2015 (currently abandoned). U.S. application Ser. No. 14/663,863 is a continuation of U.S. application Ser. No. 13/961,576, filed Aug. 7, 2013 (currently abandoned). U.S. application Ser. No. 13/961,576 is a continuation of U.S. application Ser. No. 13/676,048, filed Nov. 13, 2012 (currently abandoned). U.S. application Ser. No. 13/676,048 is a continuation of U.S. application Ser. No. 13/276,910, filed Oct. 19, 2011 (currently abandoned). U.S. application Ser. No. 13/276,910 is a continuation of U.S. application Ser. No. 12/622,264, filed Nov. 19, 2009 (currently abandoned). U.S. application Ser. No. 12/622,264 claims the benefit of U.S. Provisional Application Nos. 61/116,246, filed Nov. 19, 2008, and 61/116,252, filed Nov. 19, 2008, and is a continuation in part of U.S. application Ser. No. 12/529,001, filed Aug. 27, 2009, now U.S. Pat. No. 7,943,141, issued May 17, 2011. U.S. Pat. No. 7,943,141 is a 371 of International Application No. PCT/US2008/002626, filed Feb. 28, 2008, (currently expired), which claims the benefit of U.S. Provisional Application No. 60/892,212, filed Feb. 28, 2007.

FIELD OF THE DISCLOSURE

The present disclosure relates to polyoxazoline polymers, polyoxazoline derivatives, methods of synthesis and intermediate compounds useful in producing the foregoing, and target molecule-polyoxazoline conjugates produced using such polyoxazoline derivatives. In one embodiment, the present disclosure describes target molecule-polyoxazoline conjugates where the target molecule is a of protein or peptide, methods of synthesis for such target molecule-polyoxazoline conjugates, including enzymatic methods, and intermediate compounds useful in or produced in such methods and the biological activities of the produced polyoxazoline conjugates. The methods of the present disclosure allow for the preparation of polyoxazoline conjugates having high purity and homogeneity.

BACKGROUND

Polymer-modified therapeutics have proven to be of great utility in modern pharmaceutical science. In particular, proteins coupled to polyethylene glycols (PEGs) now constitute a number of therapeutics of great importance for treatment of a range of diseases. Due to the success of polymer-modified therapeutics, it is of interest to expand the range of polymers having such applications, especially to provide polymers having properties not possessed by polyethylene glycol.

BRIEF DESCRIPTION OF THE FIGURES

FIG. 1 illustrates the living-cation mechanism for 2-alkyl-2-oxazoline (e.g., 2-ethyl-2-oxazoline) polymerization where —OTf is —OSO$_2$—CF$_3$ or "triflate" and Nuc$^-$ is a negative nucleophile.

FIG. 3 shows the amino acid sequence of human recombinant erythropoietin.

FIG. 4 shows the effect of GCSF and 10 kDa H-PEOZ-N$^{ter}$-GCSF, 20 kDa H-PEOZ-N$^{ter}$-GCSF and 20 kDa H-PEOZ-GCSF conjugates on NSF-60 cell proliferation.

DETAILED DESCRIPTION

Definitions

Figure 2:
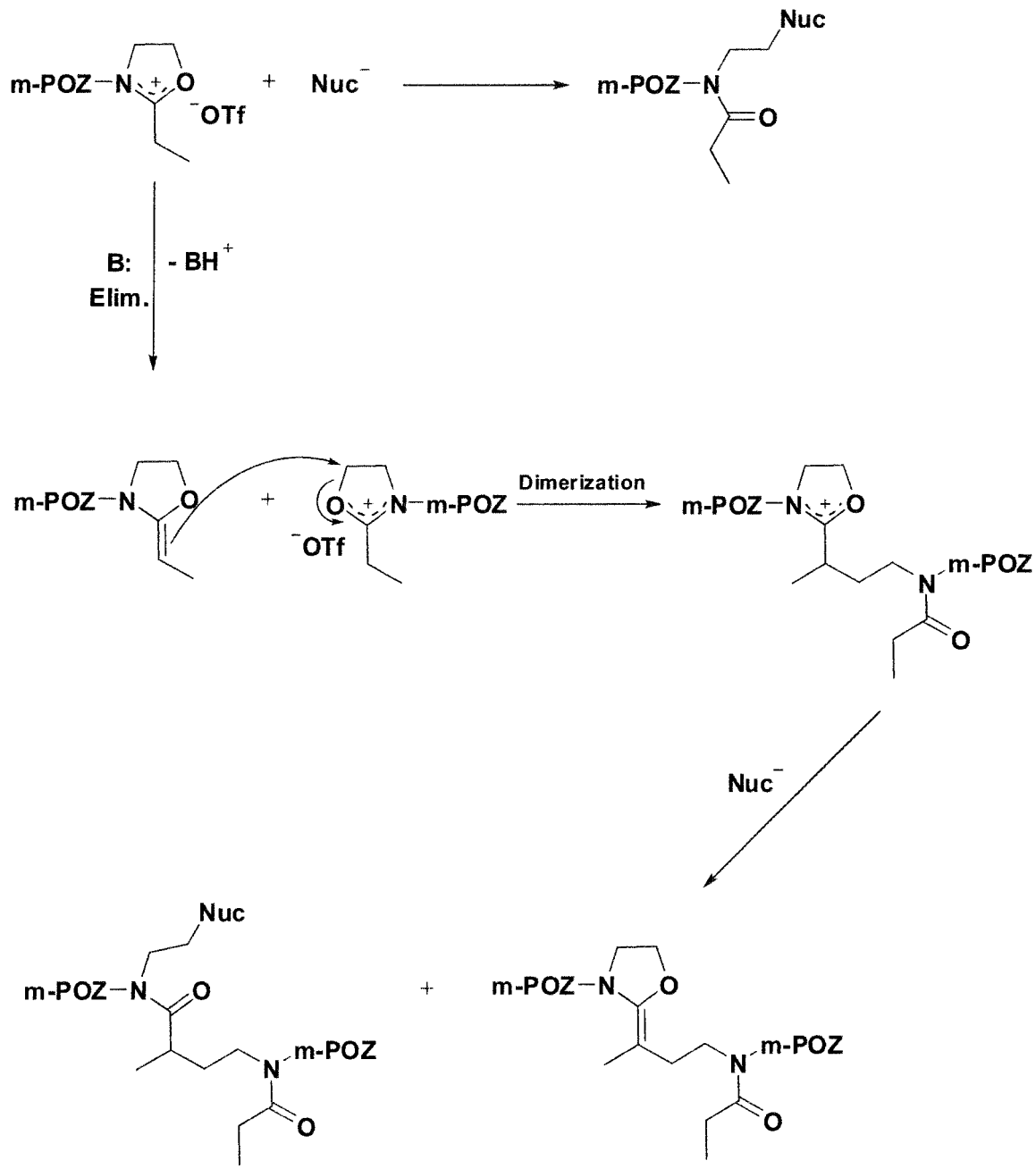
FIG. 2 shows a mechanism for the elimination-dimerization mechanism for chain transfer during polymerization of polyoxazoline derivatives, illustrated here as 2-ethyl-2-oxazoline.

As used herein, the term "POZ", "POZ compound" or "POZ polymer" refers to a polymer of 2-substituted-2-oxazoline containing a repeating unit having the structure—[N(COR$_7$)CH$_2$CH$_2$]$_n$— in which R$_7$ is independently selected for each repeating unit from an unsubstituted or substituted alkyl, alkenyl, aralkyl or heterocyclylalkyl group and n is from 3-1000; in one embodiment, the unsubstituted or substituted alkyl, alkenyl, aralkyl or heterocyclylalkyl groups comprise, from 1-10 carbon atoms, in a further specific embodiment, R$_7$ is methyl, ethyl or n-propyl.

As used herein, the term "PMOZ" refers to POZ with the repeating unit having the structure —[N(COCH$_3$)CH$_2$CH$_2$]$_n$—.

As used herein, the term "PEOZ" refers to POZ with the repeating unit having the structure —[N(COCH$_2$CH$_3$)CH$_2$CH$_2$]$_n$—.

As used herein, the term M- when used in conjunction with a POZ polymer or derivative, such as M-POZ, M-PMOZ or M-PEOZ, indicates the nitrogen on the initiating end is bound to methyl. Likewise, the term H- when used in conjunction with a POZ polymer or derivative, such as H-POZ, H-PMOZ or H-PEOZ, indicates the nitrogen on the initiating end is bound to hydrogen.

As used herein, the term "POZ derivative" or "polyoxazoline derivative" refers to a structure comprising a POZ polymer, the POZ polymer having a single active functional group on the terminal end of the POZ polymer, the functional group capable of forming a linkage, directly or indirectly, with a chemical group on a target molecule; in one embodiment the POZ derivative is a monofunctional POZ derivative.

As used herein, the term "target molecule" refers to any molecule having therapeutic, diagnostic application or a targeting function, wherein the target molecule is capable of reacting with an active functional group on a POZ polymer or a POZ derivative of the present disclosure, including, but not limited to, a therapeutic moiety (such as but not limited to a drug), a diagnostic moiety, a targeting moiety, an organic small molecule, a lipid, an oligonucleotide, a polypeptide, an antibody, an antibody fragment and a protein. Exemplary target molecules include, but are not limited to, lipids, erythropoietin, granulocyte colony stimulating factor, dynorphin A. lysozyme, human growth hormone, apomyoglobin and hyaluronic acid.

As used herein, the term "hydrolytically stable target molecule-POZ conjugate" refers to a conjugate of a POZ derivative of the present disclosure and a target molecule, such that all the chemical linkages between the POZ conjugate and the target molecule are hydrolytically stable.

As used herein, the term "hydrolytically stable" refers to a linkage that is stable in aqueous solutions under physiological conditions; in one embodiment, such linkages are stable for at least 12 hours, 24 hours, 48 hours, 96 hours, 192 hours or greater; in an alternate embodiment such linkages are stable indefinitely.

As used herein, the term "hydrolytically unstable" refers to a linkage that is not stable in aqueous solutions under physiological conditions.

As used herein, the term "physiological conditions" refers to an aqueous solution having a pH from 6-8 and a temperature from 30-42 degrees Celsius.

As used herein, the term "active functional group" refers to those groups that react readily with electrophilic or nucleophilic groups or that react readily by cylcoaddition reactions, in contrast to those groups that require strong catalysis, high temperatures or impractical reaction conditions in order to react.

As used herein, the term "link", "linked" "linkage" or "linker" when used with respect to a POZ derivative described herein, or components thereof, refers to groups or bonds that normally are formed as the result of a chemical reaction and typically are covalent linkages.

As used herein, the term "protected" with respect to hydroxyl groups, amine groups, sulfhydryl groups and other reactive groups refers to forms of these functionalities which are protected from undesirable reaction with a protecting group known to those skilled in the art such as those set forth in Protective Groups in Organic Synthesis, Greene, T. W.; Wuts, P. G. M., John Wiley & Sons, New York, N.Y., (3rd Edition, 1999) which can be added or removed using the procedures set forth therein. Examples of protected hydroxyl groups include, but are not limited to, silyl ethers such as those obtained by reaction of a hydroxyl group with a reagent such as, but not limited to, t-butyldimethyl-chlorosilane, trimethylchlorosilane, triisopropylchlorosilane, triethylchlorosilane; substituted methyl and ethyl ethers such as, but not limited to methoxymethyl ether, methythiomethyl ether, benzyloxymethyl ether, t-butoxymethyl ether, 2-methoxyethoxymethyl ether, tetrahydropyranyl ethers, 1-ethoxyethyl ether, allyl ether, benzyl ether; esters such as, but not limited to, benzoylformate, formate, acetate, trichloroacetate, and trifluoracetate. Examples of protected amine groups include, but are not limited to, amides such as, formamide, acetamide, trifluoroacetamide, and benzamide; imides, such as phthalimide, and dithiosuccinimide; and others. Examples of protected sulfhydryl groups include, but are not limited to, thioethers such as S-benzyl thioether, and S-4-picolyl thioether; substituted S-methyl derivatives such as hemithio, dithio and aminothio acetals; and others.

As used herein, the term "alkyl", whether used alone or as part of a substituent group, includes straight hydrocarbon groups comprising from one to twenty carbon atoms. Thus the phrase includes straight chain alkyl groups such as methyl, ethyl, propyl, butyl, pentyl, hexyl, heptyl, octyl, nonyl, decyl, undecyl, dodecyl and the like. The phrase also includes branched chain isomers of straight chain alkyl groups, including but not limited to, the following which are provided by way of example: —$CH(CH_3)_2$, —$CH(CH_3)$ ($CH_2CH_3$), —$CH(CH_2CH_3)_2$, —$C(CH_3)_3$, —$C(CH_2CH_3)_3$, —$CH_2CH(CH_3)_2$, —$CH_2CH(CH_3)(CH_2CH_3)$, —$CH_2CH(CH_2CH_3)_2$, —$CH_2C(CH_3)_3$, —$CH_2C(CH_2CH_3)_3$, —$CH(CH_3)CH(CH_3)(CH_2CH_3)$, —$CH_2CH_2CH(CH_3)_2$, —$CH_2CH_2CH(CH_3)(CH_2CH_3)$, —$CH_2CH_2CH(CH_2CH_3)_2$, —$CH_2CH_2C(CH_3)_3$, —$CH_2CH_2C(CH_2CH_3)_3$, —$CH(CH_3)CH_2CH(CH_3)_2$, —$CH(CH_3)CH(CH_3)CH(CH_3)CH(CH_3)_2$, —$CH(CH_2CH_3)CH(CH_3)CH(CH_3)(CH_2CH_3)$, and others. The phrase also includes cyclic alkyl groups such as cyclopropyl, cyclobutyl, cyclopentyl, cyclohexyl, cycloheptyl, and cyclooctyl and such rings substituted with straight and branched chain alkyl groups as defined above. The phrase also includes polycyclic alkyl groups such as, but not limited to, adamantyl norbornyl, and bicyclo[2.2.2]octyl and such rings substituted with straight and branched chain alkyl groups as defined above.

As used herein, the term "alkenyl", whether used alone or as part of a substituent group, includes an alkyl group having at least one double bond between any two adjacent carbon atoms.

As used herein, the term "alkynyl", whether used alone or as part of a substituent group, includes an alkyl group having at least one triple bond between any two adjacent carbon atoms.

As used herein, the term "unsubstituted alkyl", "unsubstituted alkenyl" and "unsubstituted alkynyl" refers to alkyl, alkenyl and alkynyl groups that do not contain heteroatoms.

The phrase "substituted alkyl", "substituted alkenyl" and "unsubstituted alkynyl" refers to alkyl alkenyl and alkynyl groups as defined above in which one or more bonds to a carbon(s) or hydrogen(s) are replaced by a bond to non-hydrogen or non-carbon atoms such as, but not limited to, an oxygen atom in groups such as alkoxy groups and aryloxy groups; a sulfur atom in groups such as, alkyl and aryl sulfide groups, sulfone groups, sulfonyl groups, and sulfoxide groups; a silicon atom in groups such as in trialkylsilyl groups, dialkylarylsilyl groups, alkyldiarylsilyl groups, and triarylsilyl groups; and other heteroatoms in various other groups.

As used herein, the term "unsubstituted aryl" refers to monocyclic or bicyclic aromatic hydrocarbon groups having 6 to 12 carbon atoms in the ring portion, such as, but not limited to, phenyl, naphthyl, anthracenyl, biphenyl and diphenyl groups, that do not contain heteroatoms. Although the phrase "unsubstituted aryl" includes groups containing condensed rings such as naphthalene, it does not include aryl groups that have other groups such as alkyl or halo groups bonded to one of the ring members, as aryl groups such as tolyl are considered herein to be substituted aryl groups as described below. Unsubstituted aryl groups may be bonded to one or more carbon atom(s), oxygen atom(s), nitrogen atom(s), and/or sulfur atom(s) in the parent compound, however.

As used herein, the term "substituted aryl group" has the same meaning with respect to unsubstituted aryl groups that substituted alkyl groups had with respect to unsubstituted alkyl groups. However, a substituted aryl group also includes aryl groups in which one of the aromatic carbons is bonded to one of the non-carbon or non-hydrogen atoms, such as, but not limited to, those atoms described above with respect to a substituted alkyl, and also includes aryl groups in which one or more aromatic carbons of the aryl group is bonded to a substituted and/or unsubstituted alkyl, alkenyl, or alkynyl group as defined herein. This includes bonding arrangements in which two carbon atoms of an aryl group are bonded to two atoms of an alkyl or alkenyl, group to define a fused ring system (e.g. dihydronaphthyl or tetrahydronaphthyl). Thus, the phrase "substituted aryl" includes, but is not limited to tolyl, and hydroxyphenyl among others.

As used herein, the term "unsubstituted aralkyl" refers to unsubstituted alkyl or alkenyl groups as defined above in which a hydrogen or carbon bond of the unsubstituted or substituted alkyl or alkenyl group is replaced with a bond to a substituted or unsubstituted aryl group as defined above. For example, methyl ($CH_3$) is an unsubstituted alkyl group. If a hydrogen atom of the methyl group is replaced by a bond to a phenyl group, such as if the carbon of the methyl were bonded to a carbon of benzene, then the compound is an unsubstituted aralkyl group (i.e., a benzyl group).

As used herein, the term "substituted aralkyl" has the same meaning with respect to unsubstituted aralkyl groups that substituted aryl groups had with respect to unsubstituted aryl groups. However, a substituted aralkyl group also includes groups in which a carbon or hydrogen bond of the alkyl part of the group is replaced by a bond to a non-carbon or a non-hydrogen atom.

As used herein, the term "unsubstituted heterocyclyl" refers to both aromatic and nonaromatic ring compounds including monocyclic, bicyclic, and polycyclic ring compounds such as, but not limited to, quinuclidyl, containing 3 or more ring members of which one or more is a heteroatom such as, but not limited to, N, O, and S. Although the phrase "unsubstituted heterocyclyl" includes condensed heterocyclic rings such as benzimidazolyl, it does not include heterocyclyl groups that have other groups such as alkyl or halo groups bonded to one of the ring members, as compounds such as 2-methylbenzimidazolyl are "substituted heterocyclyl" groups as defined below. Examples of heterocyclyl groups include, but are not limited to: unsaturated 3 to 8 membered rings containing 1 to 4 nitrogen atoms such as, but not limited to pyrrolyl, pyrrolinyl, imidazolyl, pyrazolyl, pyridyl, dihydropyridyl, pyrimidyl, pyrazinyl, pyridazinyl, triazolyl, tetrazolyl; saturated 3 to 8 membered rings containing 1 to 4 nitrogen atoms such as, but not limited to, pyrrolidinyl, imidazolidinyl, piperidinyl, piperazinyl; condensed unsaturated heterocyclic groups containing 1 to 4 nitrogen atoms such as, but not limited to, indolyl, isoindolyl, indolinyl, indolizinyl, benzimidazolyl, quinolyl, isoquinolyl, indazolyl, benzotriazolyl; unsaturated 3 to 8 membered rings containing 1 to 2 oxygen atoms and 1 to 3 nitrogen atoms such as, but not limited to, oxazolyl, isoxazolyl, oxadiazolyl; saturated 3 to 8 membered rings containing 1 to 2 oxygen atoms and 1 to 3 nitrogen atoms such as, but not limited to, morpholinyl; unsaturated condensed heterocyclic groups containing 1 to 2 oxygen atoms and 1 to 3 nitrogen atoms, for example, benzoxazolyl, benzoxadiazolyl, benzoxazinyl (e.g. 2H-1,4-benzoxazinyl etc.); unsaturated 3 to 8 membered rings containing 1 to 3 sulfur atoms and 1 to 3 nitrogen atoms such as, but not limited to, thiazolyl, isothiazolyl, thiadiazolyl (e.g. 1,2,3-thiadiazolyl, 1,2,4-thiadiazolyl, 1,3,4-thiadiazolyl, 1,2,5-thiadiazolyl, etc.); saturated 3 to 8 membered rings containing 1 to 2 sulfur atoms and 1 to 3 nitrogen atoms such as, but not limited to, thiazolodinyl; saturated and unsaturated 3 to 8 membered rings containing 1 to 2 sulfur atoms such as, but not limited to, thienyl, dihydrodithiinyl, dihydrodithionyl, tetrahydrothiophene, tetrahydrothiopyran; unsaturated condensed heterocyclic rings containing 1 to 2 sulfur atoms and 1 to 3 nitrogen atoms such as, but not limited to, benzothiazolyl, benzothiadiazolyl, benzothiazinyl (e.g. 2H-1,4-benzothiazinyl, etc.), dihydrobenzothiazinyl (e.g. 2H-3,4-dihydrobenzothiazinyl, etc.), unsaturated 3 to 8 membered rings containing oxygen atoms such as, but not limited to furyl; unsaturated condensed heterocyclic rings containing 1 to 2 oxygen atoms such as benzodioxolyl (e.g. 1,3-benzodioxoyl, etc.); unsaturated 3 to 8 membered rings containing an oxygen atom and 1 to 2 sulfur atoms such as, but not limited to, dihydrooxathiinyl; saturated 3 to 8 membered rings containing 1 to 2 oxygen atoms and 1 to 2 sulfur atoms such as 1,4-oxathiane; unsaturated condensed rings containing 1 to 2 sulfur atoms such as benzothienyl, benzodithiinyl; and unsaturated condensed heterocyclic rings containing an oxygen atom and 1 to 2 oxygen atoms such as benzoxathiinyl. Heterocyclyl group also include those described above in which one or more S atoms in the ring is double-bonded to one or two oxygen atoms (sulfoxides and sulfones). For example, heterocyclyl groups include tetrahydrothiophene, tetrahydrothiophene oxide, and tetrahydrothiophene 1,1-dioxide. Preferred heterocyclyl groups contain 5 or 6 ring members. More preferred heterocyclyl groups include morpholine, piperazine, piperidine, pyrrolidine, imidazole, pyrazole, 1,2,3-triazole, 1,2,4-triazole, tetrazole, thiomorpholine, thiomorpholine in which the S atom of the thiomorpholine is bonded to one or more O atoms, pyrrole, homopiperazine, oxazolidin-2-one, pyrrolidin-2-one, oxazole, quinuclidine, thiazole, isoxazole, furan, and tetrahydrofuran.

As used herein, the term "substituted heterocyclyl" has the same meaning with respect to unsubstituted heterocyclyl groups that substituted alkyl groups had with respect to unsubstituted alkyl groups. However, a substituted heterocyclyl group also includes heterocyclyl groups in which one of the carbons is bonded to one of the non-carbon or non-hydrogen atom, such as, but not limited to, those atoms described above with respect to a substituted alky and substituted aryl groups and also includes heterocyclyl groups in which one or more carbons of the heterocyclyl group is bonded to a substituted and/or unsubstituted alkyl, alkenyl or aryl group as defined herein. This includes bonding arrangements in which two carbon atoms of an heterocyclyl group are bonded to two atoms of an alkyl, alkenyl, or alkynyl group to define a fused ring system. Examples, include, but are not limited to, 2-methylbenzimidazolyl, 5-methylbenzimidazolyl, 5-chlorobenzthiazolyl, 1-methyl piperazinyl, and 2-chloropyridyl among others.

As used herein, the term "unsubstituted heterocyclylalkyl" refers to unsubstituted alkyl or alkenyl groups as defined above in which a hydrogen or carbon bond of the unsubstituted alkyl or alkenyl group is replaced with a bond to a substituted or unsubstituted heterocyclyl group as defined above. For example, methyl ($CH_3$) is an unsubstituted alkyl group. If a hydrogen atom of the methyl group is replaced by a bond to a heterocyclyl group, such as if the carbon of the methyl were bonded to carbon 2 of pyridine (one of the carbons bonded to the N of the pyridine) or carbons 3 or 4 of the pyridine, then the compound is an unsubstituted heterocyclylalkyl group.

As used herein, the term "substituted heterocyclylalkyl" has the same meaning with respect to unsubstituted heterocyclylalkyl groups that substituted aryl groups had with respect to unsubstituted aryl groups. However, a substituted heterocyclylalkyl group also includes groups in which a non-hydrogen atom is bonded to a heteroatom in the heterocyclyl group of the heterocyclylalkyl group such as, but not limited to, a nitrogen atom in the piperidine ring of a piperidinylalkyl group.

General Description

Polyoxazolines (POZ) are polymers prepared from 2-substituted-2-oxazoline monomers. These polymers are water soluble and have been reported to be nontoxic in mammalian model systems. POZ is generally prepared by reaction of the appropriate stoichiometric amount of 2-alkyl-2-oxazoline with an electrophilic initiator, such as methyl p-toluene-sulfonate (or "tosylate", $CH_3-OSO_2-C_6H_4-CH_3$) or methyl triflate ($CH_3-OSO_2-CF_3$), followed by termination with a nucleophile such as hydroxide or an amine. The polymer produced is conveniently described in shorthand with the initiating group designated by the leftmost group and the terminating group designated by the rightmost group, with the 2-alkyl-2-oxazoline component in the middle. Therefore, when this shorthand description is used in the current specification, it is intended that the left side of the designation presents the "initiator end" and the right side of the designation presents the "terminal end", unless designated otherwise.

For example, when the 2-substituted-2-oxazoline is 2-methyl-2-oxazoline, methyl tosylate is used as the initiator and hydroxide is used as the terminator, the following polymer is produced:

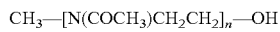

$CH_3-[N(COCH_3)CH_2CH_2]_n-OH$

The polymer above is conveniently described in shorthand notation as M-PMOZ-OH, in which the methyl initiator is designated by the leftmost M (at the initiator end), PMOZ represents polymethyloxazoline with the methyl of the repeating unit designated by the M of PMOZ, and the terminating hydroxyl is designated by the —OH (at the terminal end). The degree of polymerization, n, can range from approximately 3 to about 1000.

Another commonly used monomer is 2-ethyl-2-oxazoline, which with methyl triflate initiation and hydroxide termination would provide the following POZ polymer:

$CH_3-[N(COCH_2CH_3)CH_2CH_2]_n-OH$

The polymer above is conveniently described in shorthand notation as M-PEOZ-OH, in which the methyl initiator is designated by the leftmost M (at the initiator end), PEOZ represents polymethyloxazoline with the ethyl of the repeating unit designated by the E of PEOZ, and the terminating hydroxyl is designated by the —OH (at the terminal end).

More complex electrophiles and nucleophiles can be used. For example, initiation of 2-ethyl-2-oxazoline polymerization with benzyl bromide and termination with excess ethylene diamine yields the following polymer:

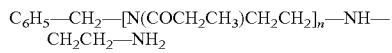

$C_6H_5-CH_2-[N(COCH_2CH_3)CH_2CH_2]_n-NH-CH_2CH_2-NH_2$

Also, different monomers can be used in the same polymer to yield various random and block copolymers.

The polymerization process is referred to as a living, cationic polymerization since initiation with an electrophile produces an oxazolinium cation that then reacts in a chain reaction with additional monomer units to produce a growing, "living" cation.

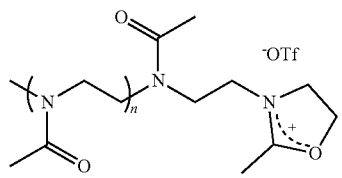

One can predict the products of termination by assuming that the living cation can be represented in the following non-cyclic form, although in reality the cyclic form is certainly the most important, and the desired products are produced by nucleophilic attack on the 5-position of the ring:

$CH_3-[N(COCH_3)CH_2CH_2]_n-N(COCH_3)CH_2CH_2^+$

In the current disclosure this cation will be represented as M-PMOZ$^+$. As noted above, this POZ cation can be "terminated" by reacting with nucleophiles such as hydroxide or amines. Interestingly, termination with the weak nucleophile water does not give the desired product of 5-attack (the "thermodynamic" product) but rather gives attack in the 2-position (the "kinetic" product). This kinetic product is not stable and can rearrange to give an ester product or undergo reversal to cation (O. Nuyken, G. Maier, A. Gross, Macromol. Chem. Phys. 197, 83-85 (1996)).

Hydroxyl terminated polymers can be further modified to give desired derivatives. For example, Zalipsky reacted the terminal —OH with glutaric anhydride to give a POZ terminated with a glutarate group (M. C. Woodle, C. M. Engbers and S. Zalipsky, Bioconjugate Chem., 1994, 5, 493-496).

$M-PMOZ-O_2C-CH_2CH_2CH_2-CO_2H$

The above polymer was activated as the succinimidyl ester and coupled to phospholipids and used to prepared POZ-modified liposomes. These liposomes were found to have similar properties to PEG-modified liposomes.

Amine terminated polymers also provide useful reactive groups for further derivatization. For example, termination with methyl amine gives a POZ terminated with the active group —NHCH$_3$. Termination with the cyclic diamine piperazine can also be useful.

Oxazoline polymerizations can also be initiated with functional nucleophiles. For example, the electrophilic initiator ethyl 3-bromopropionate has been used to initiate 2-ethyl-2-oxazoline polymerization. Termination with hydroxide gives the following polymer:

$HO_2C-CH_2CH_2-[N(COCH_2CH_3)CH_2CH_2]_n-OH$

It is noteworthy that POZs having the same functional group on the initiator end and the terminal end are chemically different because the group at the initiator end is attached to nitrogen while the group at the terminal end is attached to carbon. For example, the following two polymers are both propionic acid derivatives of PMOZ but differ in that the propionic acid at the initiator end is attached to nitrogen and the propionic acid at the terminal end is attached to carbon (the beginning or ending monomer unit is shown for clarity):

$HOOCCH_2CH_2-N(COCH_3)CH_2CH_2-PMOZ-OH$

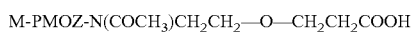

$M-PMOZ-N(COCH_3)CH_2CH_2-O-CH_2CH_2COOH$

Yet another route to preparing polyoxazolines with active functional groups is to copolymerize a monomer such as 2-ethyl-2-oxazoline with an oxazoline monomer having an active functional group in the 2-position. For example, Jordan and colleagues have prepared oxazolines with acetylenes and protected aldehydes, carboxylic acids and amines in the 2-position (F. C. Gaertner, R. Luxenhofer, B. Blechert, R. Jordan and M. Essler, J. Controlled Release, 2007, 119, 291-300). Copolymerization of these functional monomers with 2-ethyl-2-oxazoline gives random copolymers with multiple pendent or side-chain active functional groups. For example, initiation with methyl triflate of polymerization of 2-ethyl-2-oxazoline and 2-pentynyl-2-oxazoline, followed by termination with piperazine (NHC$_4$H$_8$NH) gives the following random copolymer:

CH$_3$—{[N(COCH$_2$CH$_3$)CH$_2$CH$_2$]$_n$—[N(COCH$_2$CH$_2$—CCH)CH$_2$CH$_2$]$_m$}$_{ran}$—NC$_4$H$_8$NH The subscript "ran" indicates that the polymer is a random copolymer. Values of n are typically around 20-30 while m is around 2-5.

To couple a POZ to a target molecule, such as, but not limited to, a polypeptide, it is necessary to "activate" the polymer by attaching an active functional group to at least one terminus of the polymer that is capable of forming a linkage with a group on the target molecule. There has been little work done on activation of POZ for coupling to target molecules. The active group may be added at the initiator (left) end or terminal (right) end, or both. For example, when the target molecule is a polypeptide, the polypeptide has a number of amino groups on the surface that can react with the active functional group on the POZ, and in the only published example of attachment of POZ to a protein, Myamoto and colleagues attached the POZ below to amino groups of the enzyme catalase (M. Myamoto, T. Saegusa, et al., Macromolecules, 1990, 23, 3201-3205):

M-PMOZ-O$_2$C—CH$_2$CH$_2$CH$_2$—CO$_2$—NHS

In this case M-PMOZ-OH was reacted with glutaric anhydride, and the resulting carboxylic acid was activated with N-hydroxysuccinimide, which is represented as NHS. NHS active esters are commonly used active forms of carboxylic acids. In this example the POZ-catalase conjugate proved to be active.

The prior art has described three terminally-activated POZ compounds capable of being conjugated to a target molecule. However, each of the previously described POZ derivatives suffers from limitations. Zalipsky described an activated propionic acid POZ compound, NHS—OOCCH$_2$CH$_2$-PEOZ-OH where the activating group was attached to the initiator end of the molecule (S. Zalipsky, C. B. Hansen, J. M. Oaks and T. M. Allen, J. Pharm. Sci., 85, 133-137 (1996)). The POZ compound was made by initiation of polymerization using a moiety containing the activating group. However, Jordan, Hoogenboom and others have shown that initiation of polymerization with different activating groups can require greatly differing reaction conditions requiring extensive studies to determine optimal reaction conditions. Thus if one chooses the initiator method to make activated POZ compounds, one must conduct exploratory work to determine appropriate reaction conditions for each new compound. Also the above compound is difunctional since it is terminated with a hydroxyl group rather than an inert group such as an alkyl group. Also, as discussed below, initiation of polymerization with an alkyl halide does not proceed by a living-cation mechanism and thus high polydispersities are found.

The NHS-activated glutarate derivative has been made by Myamoto and Zalipsky. This derivative was prepared from a monofunctional POZ polymer having an OH group as the terminal activating group (M-PMOZ-OH). However, glutarate and succinate derivatives have a hydrolytically unstable ester linkage connecting the target molecule to the POZ compound. For example, the NHS-activated glutarate derivative will react with a target molecule, illustrated here as a protein, as shown:

M-PMOZ-O$_2$C—CH$_2$CH$_2$CH$_2$—CO$_2$—NHS+PROTEIN-NH$_2$→

→M-PMOZ-O$_w$C—CH$_2$CH$_2$CH$_2$CH$_2$—CONH—PROTEIN

As a result of the hydrolytically unstable ester linkage, the target molecule-POZ conjugate produced will not be stable in a biological system under physiological conditions, such as a human or other mammal, but will hydrolyze to cleave the POZ from the protein:

M-PMOZ-O$_2$C—CH$_2$CH$_2$CH$_2$—CONH—PROTEIN→

→M-PMOZ-OH+HO$_2$C—CH$_2$CH$_2$CH$_2$—CONH-PROTEIN

Furthermore, in the scheme above, when the target molecule-POZ conjugate undergoes hydrolysis due to the cleavage of the unstable ester linkage, the resulting target molecule will contain a "tag" or "hapten" which can lead to immunogenicity of the target molecule.

Finally, the orthopyridyl disulfide (OPSS) derivative has been made (G. Hsiue, et al., Bioconjugate Chem., 2006, 17, 781-786). This derivative could in theory be coupled to a protein thiol group to give a disulfide linkage, although this was not done by Hsiue, but it is known that disulfides are unstable and subject to ready reduction in plasma.

An additional problem hindering use of known POZ polymers for modification of target molecules is that some POZ polymers do not possess a single active functional group; i.e., they are not "monofunctional". Monofunctionality is necessary if one seeks to avoid crosslinking and or incorporation of multiple target molecules on the polymer backbone. For example, Jordan and his colleagues have published work showing copolymerization of 2-ethyl-2-oxazoline with oxazoline monomers containing functional groups. These pendent functional groups are capable in some instances of being coupled to peptides. However, this technique was not designed to provide monofunctional POZ polymers but rather produces multifunctional compounds with pendent groups along the backbone. Having multiple functional groups present in the POZ backbone can be advantageous in some instances, but would lead to crosslinking and aggregate formation when coupling with multifunctional target molecules, such as, but not limited to, polypeptides and proteins. Also there are instances when one would desire to have a single target molecule coupled to a polymer, and multi-functional POZ polymers will not permit this.

Some of the above functional POZ compounds have the potential to be coupled to target molecules such as proteins and small molecule drugs. However, as work with polyethylene glycol-modified therapeutics has shown, it is frequently necessary for commercial development of polymer-modified drugs to utilize polymers with molecular weights (MWs) as high as 40,000 Da or higher and with molecular weight distributions or polydispersities (PDs) of less than 1.1. There has been a great deal of work showing that MWs and PDs in the above range cannot be achieved for POZ with conventional techniques. It is generally seen that as the molecular weight of growing POZ chains reaches approximately 5,000 Da, the polydispersity increases appreciably. Side reactions, including chain transfer, begin to grow in importance. Use of unusually low polymerization temperatures combined with reaction times of several weeks has been shown to give acceptable PDs, but such conditions are not practical for commercial-scale preparations (J. S. Park and K. Kataoka, Macromolecules, 39, 6622 (2006)). Hoogenboom, Schubert and colleagues indicate that low-PD POZ can be prepared by using microwave irradiation, but again commercial-scale polymerizations are not available with this technique (R. M. Paulus, T. Erdmenger, C. R.

Becer, R. Hoogenboom and U. S. Schubert, Macromol. Rapid Comm., 28, 484-491 (2007)). As a consequence of the generally found broad polydispersities, the functional POZ compounds described to date are seriously limited for use in polymer therapeutics.

Yet another problem hindering use of POZ derivatives in modification of target molecules is the unavailability of a range of appropriate activated POZ molecules capable of reaction with the target molecules under a range of conditions. Furthermore, the POZ molecules presently available are multifunctional or contain hydrolytically unstable bonds when conjugated to target molecules, with the disadvantages associated therewith, or the active substituent is added during the initiation reaction, with the disadvantages associated therewith. Furthermore, pendent functionality has been described, but these derivatives are multifunctional and not suitable for the current application.

SUMMARY OF THE INVENTION

The present disclosure provides monofunctional POZ derivatives having a range of active groups allowing conjugation of the monofunctional POZ derivatives to a wide range of target molecules under a wide range of reaction conditions to produce a hydrolytically stable target molecule-POZ conjugate; in certain embodiments, one target molecule is bound to the POZ derivative. The ability to provide monofunctional POZ derivatives with a range of active groups capable of reacting with a selected group on a target molecule under different reaction conditions provides a significant advantage over the prior art since different target molecules are sensitive to different reaction conditions and the most effective reaction conditions for conjugation of a POZ derivative to a target molecule frequently vary depending on the nature of the target molecule and the group on the target molecule reacting with the POZ derivative.

The present disclosure addresses the limitations of the previously described POZ polymers by providing a range of POZ polymers and POZ derivatives not previously known in the art. Furthermore, the present disclosure provides monofunctional POZ derivatives having active functional groups on the terminal end thereof. Still further, the present disclosure addresses the limitations of the prior art by providing synthesis methods for the disclosed POZ derivatives utilizing POZ molecules with terminator end groups, such as, but not limited to, the hydroxyl group, that are readily available and can be obtained using known preparation chemistries. A wide variety of POZ derivatives can then be prepared by coupling of small, active molecules to the available terminal group in a step-wise fashion to generate the desired active functional groups on the POZ derivative (as described herein). In addition, the present disclosure addresses the limitations of the prior art by providing a hydrolytically stable target molecule-POZ conjugate through the use of the described monofunctional POZ derivatives. Such an approach increases the in vivo half-life of the target molecule-POZ conjugate and reduces the problems of immunogenicity related to "hapten tagging" of the target molecule. The disclosed monofunctional POZ derivatives, synthesis methods and resulting hydrolytically stable target molecule-POZ conjugates have not been appreciated in the art.

Therefore, the described monofunctional POZ derivatives and synthesis methods avoid the problems inherent in the art and provide a mechanism to produce hydrolytically stable target molecule-POZ conjugates in which one target molecule is bound to the POZ derivative.

Any 2-substituted-2-oxazoline compound, such as but not limited to, PMOZ and PEOZ, may be used to produce the POZ derivatives of the present disclosure, as discussed in more detail below. In certain embodiments, PEOZ or PMOZ are the 2-substituted-2-oxazolines POZ molecules. As is known in the art, different alkyl groups in the 2-alkyl-2-oxazoline molecules can provide differing solubilities, pharmacokinetics and membrane permeating abilities to the POZ derivatives described herein. In addition, the nature of the repeating unit in the POZ polymer backbone may be the same to produce a homopolymer (such as but not limited to PMOZ and PEOZ) or at least one of the repeating units may be different to provide for copolymers, such as, but not limited to, random or block copolymers.

Furthermore, the present disclosure provides novel methods for synthesizing POZ polymers with low polydispersity (PD) values and decreased amounts of impurities produced by unwanted side reactions, such as, but not limited to, chain transfer. In one embodiment, the present disclosure describes novel methods for minimizing unwanted side reactions, such as, but not limited to, chain transfer, allowing the production of POZ polymers of increased purity with low PD values. In one embodiment, the methods of the present disclosure provide for POZ derivatives with low PD values at increased MW values. In a further embodiment, POZ polymers are produced with decreased amounts of impurities. The novel methods provided for in the present disclosure are an improvement over the methods of the prior art and provide for large scale commercial preparation of POZ polymers suitable for use in modification of a wide variety of target molecules.

Therefore, the present disclosure also provides POZ polymers of increased purity and with low PD values suitable for use in pharmaceutical applications. As is known in the art, PD values will vary with MW; in general, as the molecular weight increases the PD value also increases. Using the methods of the present disclosure, POZ polymers of various MWs can be produced on commercial scale with lower PD values at a given MW than can be produced using the commercially-applicable methods of the prior art. For example, using the methods of the present disclosure, POZ derivatives of 20,000 Da MW or less can be produced with PD values of less than or equal to 1.1. In a further particular embodiment, the foregoing are produced with decreased amount of impurities. As is known in the art and illustrated in the Examples herein, POZ derivatives synthesized using the methods of the prior art exhibit certain impurities that are seen as high MW shoulders and low MW tails in GPC traces. These impurities are generated, at least in part, through unwanted side reactions, such as, but not limited to, chain transfer. As a result, the disclosed POZ derivatives are suitable for use in modification of a wide variety of target molecules.

The present disclosure also provides for new POZ-target molecule conjugates. The POZ conjugates of the present disclosure provide beneficial properties not present in prior polymer conjugates of the art. In one embodiment, the present disclosure provides methodologies of attaching POZ and/or POZ derivatives to target molecules and the resulting POZ-target molecule conjugates. In one embodiment, the POZ-target molecule conjugates are hydrolytically stable. Non-enzymatic and enzymatic methods for producing such conjugates are provided. In one embodiment, the target molecules are biopharmaceuticals and lipids. Exemplary lipids include, but are not limited to, natural lipids, such as, but not limited to, phospholipid, a glycerolipid, or a sterol lipid, as well as synthetic lipids. Exemplary target molecules include, but are not limited to, erythropoietin, granulocyte colony stimulating factor, dynorphin A. lysozyme, human growth hormone, apomyoglobin and hyaluronic acid.

Through the use of the methods described herein, a range of monofunctional POZ derivatives with different active functional groups are provided. Furthermore, the present disclosure provides synthesis methods to produce such monofunctional POZ derivatives in an efficient manner. Finally, through the use of the monofunctional POZ derivatives described, a hydrolytically stable target molecule-POZ conjugate may be produced in which one target molecule is bound to the POZ derivative.

Methods of Synthesis of POZ Derivatives With Low PD Values

The current state of the art for polymerization of 2-aryl- and 2-alkyl-2-oxazolines is derived from the publications of Kobayshi, Nuyken and Jordan (S. Kobayashi, E. Masuda, S. Shoda and Y. Shimano, Macromolecules, 1989, 22, 2878-2884; A. Gross, G. Maier and O. Nuyken, Macromol. Chem. Phys., 1996, 197, 2811-2826; and F. C. Gaertner, R. Luxenhofer, B. Blechert, R. Jordan and M. Essler, J. Controlled Release, 2007, 119, 291-300). In these methods polymerization is initiated with an electrophile, such as an alkyl tosylate or alky triflate; in one embodiment, methyl tosylate or methyl triflate is used. These strong electrophiles are used to favor polymerization by a living-cation mechanism since this mechanism, in theory, gives no termination or chain-transfer reactions (Q. Liu, M. Konas and J. S. Riffle, Macromolecules, 1993, 26, 5572-5576) (see FIG. 1). However, it is known from the prior art that chain transfer reactions do occur and that the reaction does not proceed strictly by the living cation mechanism. If weak electrophiles such as, but not limited to, alkyl halides are used, the reaction proceeds by a covalent mechanism with a consequent significant increase in PD. The prior art polymerization methods utilize chlorobenzene, dichlorobenzene or acetonitrile as solvent. The propagation phase is conducted at approximately 80° C. for approximately 1-3 days. Termination is conducted by heating at 80-90° C. with aqueous sodium carbonate to give a hydroxyl terminal group or by reacting with a secondary amine such as morpholine or piperidine to give a terminal tertiary amine.

The use of these typical, prior art methods leads to the presence of a high-MW shoulder of approximately 5-10% and significant low-MW tailing in gel permeation chromatography. Such results have been noted in the art (see J. Park and K. Kataoka, Macromolecules, 2006, 39, 6622-6630.). It is generally stated in the literature that this broadening of the MW distribution is due to chain transfer proceeding through an elimination-dimerization mechanism, although structural details and experimental support for this process are limited (M. Litt, A. Levy and J. Herz, J. Macromol. Sci.-Chem., 1975, A9, 703-727). To the extent that chain transfer reactions do occur, such reactions cannot be considered to be truly living polymerizations. Therefore, it would be beneficial to reduce the occurrence of unwanted side reactions such as chain transfer.

The applicants have clarified the details of the elimination-dimerization mechanism, provided experimental support for the mechanism, and proposed implications of the mechanism regarding the termination step. This latter advance is particularly important because it shows why certain termination reactions fail and it leads us to choose termination reactions that succeed. Such a finding has not been described in the art and it provides guidance in creating synthetic methods that minimize the occurrence of unwanted side reactions and that yield the desired terminated products.

As discussed herein, the use of the prior art methods produced a POZ product that contained a high MW shoulder of approximately 5-10% of the total mass of the POZ product. This high MW shoulder contributes to the unacceptable PD values obtained using synthetic methods of the prior art. The high MW shoulder observed in the methods of the prior art is composed, at least in part, of a high-MW dimer that is formed during the polymerization and/or termination steps (see FIG. 2). The elimination-dimerization mechanism predicts that if chain transfer occurs during the termination step, the material in the high MW shoulder would be approximately double the MW of the desired product. Furthermore, if chain transfer occurs during the propagation step, a new polymer chain will be initiated, and since monomer concentration is less at this point, the MW of this polymer will be less than that of the bulk of polymer. In addition, since this new polymer chain results from chain transfer, it must be initiated by a proton, rather than by methyl, and thus the MALDI spectrum of this polymer will show a set of peaks 14 Da less than that of the main peak.

Methods for synthesizing POZ polymers and POZ derivatives with low PD and methods of using the foregoing, as well as benefits of using the foregoing, are described in U.S. application Ser. No. 12/529,001; this application is hereby incorporated by reference for such teachings, such as pages 15-20 and the examples recited therein.

Methods of Synthesis of Monofunctional POZ Derivatives

The present disclosure provides novel methods to synthesize the described monofunctional POZ derivatives. The novel synthetic methods are referred to herein generally as the building block method. In one embodiment of the building block method, a one-step synthetic method is disclosed. In an alternate embodiment of the building block method, a two-step method is disclosed. In a further alternate embodiment of the building block method, a living polymer synthesis is described. Each of the methods will be described in more detail below. In any of the foregoing embodiment, POZ polymers and POZ derivatives with low PD values may be used.

Building Block One-Step Method

In a first embodiment of the building block approach, a one-step method is disclosed. In the one-step method, a range of monofunctional POZ derivatives is generated in a single step through reaction between a single terminally-functionalized POZ molecule and a set of compounds containing the desired active group. In this way a single terminally-functionalized POZ molecule can be converted to a range of activated monofunctional POZ derivatives. This approach means that one need only optimize the polymerization chemistry for production of a single monofunctional POZ derivative. The POZ terminal group (Y below) is chosen carefully to make possible this range of reactions to provide a range of active groups. The one-step method can be represented as follows in its general form in Scheme 1:

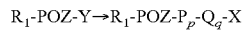   1

Scheme 1

Where

POZ is —[N(COR$_7$)CH$_2$CH$_2$]$_n$—;

R$_7$ is independently selected for each repeating unit from an unsubstituted or substituted alkyl, alkenyl or aralkyl group, in one embodiment having from 1 to 12 carbons;

R$_1$ is hydrogen or unsubstituted or substituted alkyl, alkenyl or aralkyl group groups;

R$_2$-R$_4$, R$_{11}$ and R$_{14}$-R$_{15}$ are each independently selected from hydrogen or unsubstituted or substituted alkyl, alkenyl or aralkyl group groups, in one embodiment having from 1 to 10 carbons;

$R_8$ is —$C_6H_{10}$—$CH_2$— (cyclohexylmethylene);

$R_{23}$ is unsubstituted or substituted alkyl, alkenyl, alkynyl or aralkyl group groups, in one embodiment having from 1 to 10 carbon atoms, or substituted or unsubstituted aryl groups;

Y is —OH, —SH, —S—$(CH_2)_k$—$CO_2H$, piperazinyl, substituted piperazinyl, substituted piperidinyl, or —$NHR_2$;

P is a linking group; P can be any group capable of forming the linkages shown in scheme 1 and may be selected depending on the chemistry of the groups with which it forms a linkage; representative P groups include, but are not limited to, —O—, —S—, —NH—, —$NR_{11}$— or unsubstituted heterocyclyl, such as, but not limited to, piperazinyl ($NC_4H_8N$);

Q is a linking group; Q can be any group capable of forming the linkages shown in scheme 1 and may be selected depending on the chemistry of the groups with which it forms a linkage; representative Q groups include, but are not limited to, an unsubstituted or substituted alkyl, alkenyl, heterocyclyl or aryl group, —$(CH_2)_m$—CONH—$(CH_2)_m$—, —NH—$(CH_2)_m$—NHCO—$(CH_2)_m$—, —CO—$(CH_2)_m$—, —CO—$C_6H_4$—, or —CO—$R_8$—, —$(R_{15})_m$— or —$(CR_3R_4)_m$;

n is an integer from 3 to 1000;

k and m are integers independently selected from 1 to 10;

p and q are integers independently selected from zero or one;

X is an active functional group capable of forming a linkage with a target molecule to produce a hydrolytically stable target molecule-POZ conjugate.

In one embodiment, the active functional group is selected from the following general classes of compounds: aldehydes (—CHO), active carbonates (—O—CO—Z), maleimides, sulfonate esters (—$OSO_2$—$R_{23}$), including but not limited to tresylate (2,2,2-trifluoroethanesulfonate) and mesylate (—O—$SO_2$—$CH_3$ or —OMs), hydrazides (—$CONHNH_2$), epoxides, iodoacetamides, alkynes, azides (—$N_3$), isocyanates (—OCN), cyanates (—NCO), isothiocyanates (—SCN), thiocyanates (—NCS), nitriles (—CN), carbonyldiimidazole derivatives, vinylsulfones, carboxylic acid halides, active esters (—CO—Z) and carboxylic acids (—$CO_2$—H); and Z is an activating group of which there are many known in the art including N-succinimidyloxy, chlorine, bromine, sulfo-N-succinimidyloxy, p-nitrophenoxy, 1-imidazolyl, and 1-benzotriazolyloxy;

The active functional group may also be protected to yield a protected active functional group by methods known in the art. For example, an acetal [CH($OR_{14}$)$_2$] is an exemplary protecting group, which can be hydrolyzed to produce an aldehyde group. The active functional group may be substituted with groups, such as but limited to, those groups described with respect to a substituted alkyl group and substituted and unsubstituted alkyl, alkenyl, alkynyl, aralkyl or heterocycloalkyl groups. Furthermore, the active functional group includes those compounds that may be converted to an active functional group. For example, the X group may include a compound that is modified by a linkage that is susceptible to hydrolysis under certain reaction conditions (such as those used to join the POZ derivative to a target molecule), thereby cleaving the linkage and exposing the active functional group to react with a group on the target molecule.

In Scheme 1, the reactant $R_1$-POZ-Y is the direct product of polymerization of POZ and the Y group is capable of being converted directly to a series of monofunctional POZ derivatives capable of forming a hydrolytically stable target molecule-POZ conjugate. For example, in one embodiment Y equals —OH and is obtained when the POZ polymerization reaction is terminated with hydroxide. In an alternate embodiment, Y equals —$NHR_2$ and is obtained when the POZ polymerization reaction is terminated with a compound containing an amino group, $R_2NH_2$. Other useful amine terminating agents providing useful Y groups are piperazine or a substituted piperazine such as 1-piperazinepropanol (H—$NC_4H_8N$—$CH_2CH_2CH_2$—OH) Substituted piperidines are also useful since these provide the rapid termination usual for amines, and they also introduce a range of functional groups. Commercially available substituted piperidines include 4-piperidine butyric acid, 3-piperidine carboxylic acid and 4-piperidine methanol. In an alternate embodiment, Y equals —S—$CH_2CH_2$—$CO_2H$ and is obtained with the POZ polymerization reaction is terminated with $^-$S—$CH_2CH_2$—$CO_2$—$CH_3$ (followed by hydrolysis without isolation).

Various exemplary reactions illustrating the preparation via the one-step method of $R_1$-POZ-X derivatives are illustrated below. In the reactions presented below, $R_1$ and $R_7$ are methyl and Y is —OH or —$NHR_2$, where $R_2$ is $CH_3$.

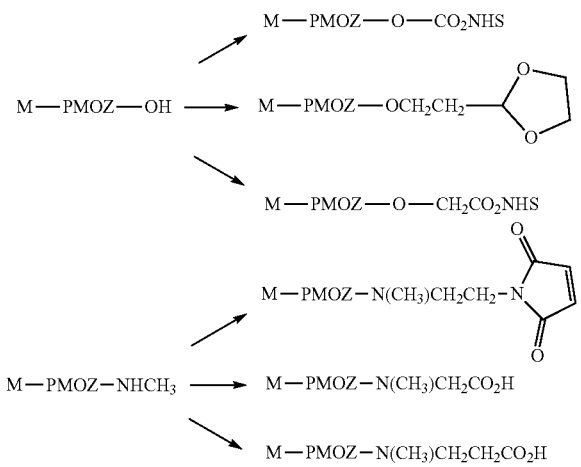

The structures above can be seen to fall within the description of Scheme 1. For example, for the active carbonate above (M-PMOZ-$OCO_2$—NHS) $R_1$ and $R_7$ are methyl, p and q are zero, and X is the succinimidyl carbonate. For the active ester above (M-PMOZ-O—$CH_2$—$CO_2NHS$) $R_1$ and $R_7$ are methyl, P is —O—, p is 1, Q is —$CH_2$—, q is 1, and X is —$CO_2NHS$.

The monofunctional POZ derivatives with the active groups described above provide a number of useful and differing properties, allowing for the selection of a particular monofunctional POZ derivative with a desired active functional group based on the nature of the target molecule and the desired reaction conditions. For example, when the active functional group is an aldehyde, the monofunctional POZ derivative reacts predominately with the N-terminal amine of the target molecule in a defined pH range to form an imine (which is typically reduced with borohydride to a secondary amine). When the active functional group is an active ester, the monofunctional POZ derivative reacts predominately with amines, including, but not limited to, nonterminal lysine groups on the target molecule. Likewise, when the active functional group is an active carbonate or tresylate, the monofunctional POZ derivative reacts readily with amines, but with reaction conditions and selectivity different from active esters and aldehyde. Furthermore, when the active functional group is a vinylsulfone or maleimide the monofunctional POZ derivative reacts predominately with thiols, but the reaction conditions differ for each of these groups, providing a range of reaction conditions appropriate for a range of target molecules.

Importantly, each of the monofunctional POZ derivatives formed using the synthetic scheme above is capable of forming a hydrolytically stable target molecule-POZ conjugate.

Building Block Two-Step Method

In an alternative embodiment, a two-step synthesis method is disclosed. In the first step of the two-step method, an initial polymer product ($R_1$-POZ-Y, below), prepared by polymerization as described above, is reacted with a desired compound to produce a POZ intermediate ($R_1$-POZ-Y', below). In the second step of the two-step method, this POZ intermediate is further reacted with a range of compounds comprising a range of active functional groups to form a series of monofunctional POZ derivatives ($R_1$-POZ-X, below) capable of forming hydrolytically stable target molecule-POZ conjugates. The two-step synthetic method offers the advantage of providing a range of monofunctional POZ derivatives using only two reactions and starting from a single initial polymer product ($R_1$-POZ-Y), thus minimizing the need to optimize polymerization conditions for multiple polymer products. The two-step method provides monofunctional POZ derivatives not available by the one-step method. In its most general form, the transformations of the building block two-step method are illustrated in Scheme 2 below.

$$P_1POZ\text{-}Y \rightarrow R_1\text{-}POZ\text{-}Y' \rightarrow R_1\text{-}POZ\text{-}X \qquad \text{II}$$

Scheme 2

The building block two-step method can be presented in a detailed form as follows in Scheme 3. In Scheme 3, Y' is an active group, including, but not limited to, active esters and active carbonates, capable of reacting with a functional nucleophile, represented by the T group.

Step 1

$R_1$-POZ-Y→$R_1$-POZ-$P_p$-$Q_q$-Y'

Step 2

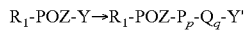
$R_1$-POZ-$P_p$-$Q_q$-Y'+T-$U_u$-X→$R_1$-POZ-$P_p$-$Q_q$-$W_w$-$U_u$-X    III Scheme 3
Where
 $R_1$-$R_4$, $R_7$, $R_8$, $R_{11}$, $R_{14}$-$R_{15}$, $R_{23}$, POZ, P, Q, k, m, n, p, q, Y, and X are as described above;
 U is a linking group; U can be any group capable of forming the linkages shown in scheme 3 and may be selected depending on the chemistry of the groups with which it forms a linkage; representative U groups include, but are not limited to, including, but not limited to —($R_{16}$)$_o$—, —(C$R_5R_6$)$_o$—, —NH—$R_{21}$—NHCO—$R_{22}$—;
 o is an integer from one to ten;
 w and u are integers independently selected from one or zero;
 $R_5$, $R_6$, $R_{16}$, $R_{21}$ and $R_{22}$ are each independently selected from hydrogen or unsubstituted or substituted alkyl, alkenyl or aralkyl groups, in one embodiment having from 1 to 10 carbon atoms;
 $R_{17}$ is selected from hydrogen or unsubstituted or substituted alkyl, alkenyl or aralkyl group groups, in one embodiment having from 1 to 10 carbon atoms, or substituted or unsubstituted aryl groups.

Y' and T are a reactive pair that react to form in a linkage W which is hydrolytically stable, wherein the Y' and T reactive pair and the resulting W linkage are selected from those groups and linkages shown in Table 1. Y' and T groups may be reversed without affecting the nature of the W linkage.

TABLE 1

Some possible T-Y' pairs and resulting W linkages

| T group | Y' Group | W Linkage |
|---|---|---|
| —NH$_2$ | Any active carbonate (such as, but not limited to, —O—CO—O—Z) | Urethane (—NH—CO—O—) |
| —OH | isocyanate (—NCO) | Urethane (—NH—CO—O—) |
| —NH$_2$ | any active ester or acid halide (such as, but not limited to, —CO—O—Z, —CO—Cl and —CO—Br) | Amide (—NH—CO—) |
| —NH$_2$ | NCO | Urea (—NH—CO—NH—) |
| —NCS | —NH$_2$ | Thiourea (—NH—CS—NH—) |
| halides —Cl or —Br | —OH | Ether (—O—) |
| —OH | —OSO$_2$—$R_{17}$ | Ether (—O—) |
| halides | —SH | Thioether (—S—) |
| O—SO$_2$—$R_{17}$ | —SH | Thioether (—S—) |
| halides | —NH$_2$ | Amine (—NH—) |
| O—SO$_2$—$R_{17}$ | —NH$_2$ | Amine (—NH—) |
| —SH | —NCO | —S—CO—NH— |
| —SH | —OSO$_2$—$R_{17}$ | Thioether (—S—) |

An exemplary reaction illustrating the preparation of a hydrolytically stable $R_1$-POZ-$P_p$-$Q_q$-$W_w$-$U_u$-X derivative is illustrated below. In this reaction $R_1$ is hydrogen and $R_7$ is methyl, Y is —OH, p and q are zero, U is —CH$_2$CH$_2$—, u is one, the reactive pair T and Y' are —NH$_2$ and —O—CO$_2$—NHS, respectively, which form the urethane W linkage, w is one, and X is an acetal (protected aldehyde):

H-PMOZ-OH→M-PMOZ-O—CO$_2$—NHS

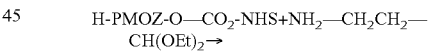
H-PMOZ-O—CO$_2$-NHS+NH$_2$—CH$_2$CH$_2$—CH(OEt)$_2$→

H-PMOZ-OCONH—CH$_2$CH$_2$—CH(OEt)$_2$, which after hydrolysis, yields

H-PMOZ-OCONH—CH$_2$CH$_2$—CHO.

Another example of Scheme 3 is illustrated below. In this reaction $R_1$ and $R_7$ are methyl, Y is —OH, P is —O—, p is one, Q is —CH$_2$CH$_2$—, q is one, the reactive pair T and Y' are —NH$_2$ and —CO$_2$H, respectively, which form the amide (—CONH) W linkage, w is one, U is —CH$_2$CH$_2$—, u is one, and X is acetal (protected aldehyde):

M-PMOZ-OH→M-PMOZ-O—CH$_2$CH$_2$—CO$_2$H

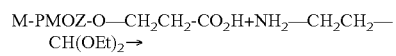
M-PMOZ-O—CH$_2$CH$_2$-CO$_2$H+NH$_2$—CH$_2$CH$_2$—CH(OEt)$_2$→

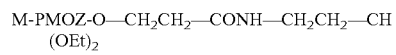
M-PMOZ-O—CH$_2$CH$_2$—CONH—CH$_2$CH$_2$—CH(OEt)$_2$ which after hydrolysis, yields

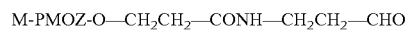
M-PMOZ-O—CH$_2$CH$_2$—CONH—CH$_2$CH$_2$—CHO

As discussed above, each of the active functional groups of Scheme 3 has unique advantages and specificities in reacting with target molecules. Furthermore, the reactivity of the T and Y' groups towards one another may be controlled through the nature of the Q and U groups. By increasing the chemical distance between the T and Y' and/or the T and X groups by increasing the size of the Q and U groups as described, the reactivity of the Y' and T groups is altered. Furthermore, the reactivity of the active functional group X towards the target molecule may be similarly modulated.

As with the one-step method, each of the monofunctional POZ derivatives formed using the two-step synthetic scheme above is capable of forming hydrolytically stable target molecule-POZ conjugates.

The Living-Polymer Method

In a further alternative embodiment of the invention, small, reactive molecules may be used to terminate oxazoline polymerization to directly provide monofunctional POZ derivatives, which can react with target molecules to form a hydrolytically stable target molecule-POZ conjugate. This method is referred to as the living polymer method. The living polymer method can be presented in its most general terms as follows in Scheme 4:

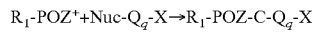

Scheme 4

Where $R_1$-$R_4$, $R_7$, $R_8$ and $R_{14}$-$R_{15}$, $R_{23}$, POZ, Q, k, m, n, q, Y, and X are as described above;

$POZ^+$ represents the cation $—[N(COR_7)CH_2CH_2]_n^+$ formed during oxazoline polymerization;

$R_{19}$ is selected from hydrogen or unsubstituted or substituted alkyl, alkenyl or aralkyl group groups, in one embodiment having from 1 to 10 carbon atoms; and Nuc is a nucleophile capable of terminating the living POZ polymerization reaction by interacting with the terminal cation $—N(COR_7)CH_2CH_2^+$ to form the hydrolytically stable linkage C, wherein the Nuc group and the resulting C linkage can be selected from those groups and linkages shown in Table 2.

TABLE 2

Some possible Nuc groups and C linkages

| Nuc Group | C Linkage |
|---|---|
| —$NHR_{19}$ | Amine (—$NR_{19}$—) |
| —SH | Thioether (—S—) |
| —$NH_2$ | Amine (—NH—) |
| piperazine | Part of ring structure |
| piperidine | Part of ring structure |

An exemplary reaction illustrating the preparation of the $R_1$-POZ-C-$Q_q$-X derivative is given below. In the reaction presented below, $R_1$ and $R_7$ are methyl, Nuc is —$NH_2$, C is —NH—, Q is —$CH_2$—, q is one, and X is —$CO_2H$ (note that the methyl ester is hydrolyzed during the reaction below):

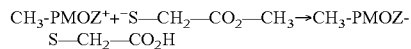

Contrary to the suggestions in the art, the present disclosure shows that cation trapping with alkoxides, such as —O—$CH_2$—$CO_2$—$CH_3$, does not result in the desired product.

As stated in Table 2, the C linkage is incorporated into the piperazine and piperidine ring structure when these compounds are used as the Nuc group. Examples of the C linkage and the structures resulting from using piperazine and piperidine as the Nuc group are provided below.

In one embodiment of this reaction, a mercaptide compound is used to terminate the oxazoline polymerization. In this method, oxazoline polymerization is initiated as described herein to form a POZ polymer with an oxazolinium cation at the terminating end of the POZ polymer. The reaction is terminated by adding a nucleophilic mercaptide molecule to the reaction, thereby terminating the living POZ polymerization. The mercaptides molecule comprises an active functional group (the active functional group may be protected as described herein) capable of reaction with a group on a target molecule to form a hydrolytically stable linkage.

In a specific embodiment of this method, the mercaptides has the structure $R_{25}S$-$D_d$-X, wherein:

X is as defined above;

$R_{25}$ is a metal; in one embodiment, $R_{25}$ is Li, Na or K;

D is a linking group, including but not limited to, an unsubstituted or substituted alkyl, alkenyl, heterocyclyl or aryl group, —$(CH_2)_b$—CONH—$(CH_2)_b$—, —NH—$(CH_2)_b$—NHCO—$(CH_2)_b$—, —CO—$(CH_2)_b$—, —CO—$C_6H_4$—, or —CO—$R_{26}$, or —$(CR_{27}R_{28})_b$;

$R_{27}$ and $R_{28}$ are each independently selected from hydrogen or unsubstituted or substituted alkyl, alkenyl or aralkyl group groups, in one embodiment having from 1 to 10 carbons;

$R_{26}$ is —$C_6H_{10}$—$CH_2$— (cyclohexylmethylene);

d is 0 or 1; and b is an integer from 1 to 10.

In one embodiment, the active functional group is a protected functional group or a compound that may be converted to an active functional group. As discussed above, each of the active functional groups has unique advantages and specificities in reacting with target molecules. As above, each of the monofunctional POZ derivatives formed using the synthetic scheme above is capable of forming a hydrolytically stable target molecule-POZ conjugate.

Specific POZ Derivatives

The present disclosure describes a variety of monofunctional POZ derivatives which can be prepared by the methods described above. Furthermore, the present disclosure describes a number of compounds useful in the synthesis of the monofunctional POZ derivatives of the present disclosure.

In one embodiment, the monofunctional POZ derivatives are described by the general formula (I), (III) or (IV):

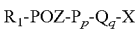           (I)

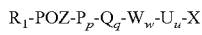           (III)

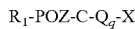           (IV)

Wherein the definitions in the general formulas (I), (II) and (III) are as provided for above with reference to Schemes 1-4.

In addition, a number of specific structures for the monofunctional POZ derivatives of the present disclosure are provided below. These structures are listed for exemplary purposes only and are not meant to limit the scope of the monofunctional POZ derivatives described herein. As above, when referred to below, the definitions provided in Schemes 1-4 above are applicable to the structures below; the definitions below also apply where applicable. In addition, for all the structures provided below, the $R_1$ group is understood to be included at the position of the initiator group (to the left of the POZ group).

$R_9$ is a linking moiety such as $—(R_{16})_O—$ or $—NH—R_{21}—NHCO—R_{22}—$;

G is an unsubstituted or substituted aryl group or a substituted or unsubstituted alkyl, alkenyl or alkynyl group, such as, but not limited to, a fluoroalkyl group; and Ar is an unsubstituted aryl or substituted aryl group.

In one embodiment, the present disclosure provides for monofunctional POZ derivatives made by the building block one-step method. Exemplary structures derived by this route include, but are not limited to, the following structures.

POZ-P—$(CR_3R_4)_m$—CH(OR$_{14})_2$
POZ-P—$(CR_3R_4)_m$—CHO and POZ-NHCO—$C_6H_4$—CHO
POZ-P—$(CR_3R_4)_m$—CO$_2$H
POZ-P—$(CR_3R_4)_m$—CO—Z
POZ-P—$(CR_3R_4)_m$—CO—NH—NH$_2$
POZ-O$_2$C—O—Z
POZ-O—SO$_2$-G

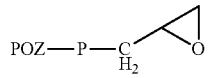

POZ-P—CH$_2$CH$_2$—SO$_2$CH=CH$_2$ and POZ-NHCO—C$_6$H$_4$—SO$_2$—CH=CH$_2$
POZ-NH—CO—C$_6$H$_4$—NHCO—CH$_2$—I
POZ-P—$(CR_3R_4)_n$—CCH In another embodiment, the present disclosure provides for monofunctional POZ derivatives made by the building block two-step method utilizing nucleophilic displacement on a POZ sulfonate ester (an intermediate derived from POZ-OH):

POZ-N$_3$
POZ-P—$(CR_3R_4)_n$—CH(OR$_{14})_2$
POZ-P—$(CR_3R_4)_m$—CHO
POZ-OCN
POZ-SCN
POZ-CN
POZ-P—$(CR_3R_4)$n-CCH
POZ-P—$(CR_3R_4)_n$—CO$_2$H and POZ-P—$(CR_3R_4)_n$—CO—Z
POZ-P—Ar—CO$_2$H and POZ-P—Ar—CO—Z In another embodiment, the present disclosure provides for monofunctional POZ derivatives made by the building block two-step method utilizing nucleophilic displacement on a POZ active carbonate (an intermediate derived from POZ-OH):

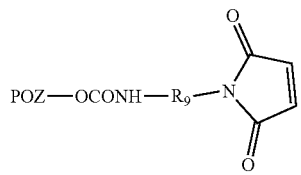

POZ-OCONH—$(CR_3R_4)_n$—CO$_2$H
POZ-OCONH—$(CR_3R_4)_n$—CO—Z
POZ-OCONH—C$_6$H$_4$—CHO

In another embodiment, the present disclosure provides for monofunctional POZ derivatives incorporating maleimides made by nucleophilic substitution on any of the above active esters:

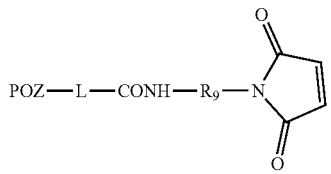

Where

POZ-L-CO— is derived from any of the herein described active carboxylate esters; and L is any of the linking moieties shown above that link POZ to the carboxyl group and includes —P—$(CR_3R_3)_m$—, —P—Ar—, and pyridinium —NC$_5$H$_4^+$—.

These maleimides can be seen to fit the above POZ-$P_p$-$Q_qW_wU_uX$ formula in which L comprises the $P_p$-$Q_q$ segment, —CONH— comprises the $W_w$ segment, and $R_9$ comprises the $U_u$ segment.

In another embodiment, the present disclosure provides for POZ derivatives made by the living cation method utilizing nucleophilic attack on the POZ cation generated during polymerization of 2-alkyl-2-oxazoline:

POZ-P—$(CR_3R_4)_n$—CO$_2$H
POZ-P—Ar—CO$_2$H and POZ-P—Ar—CO—Z

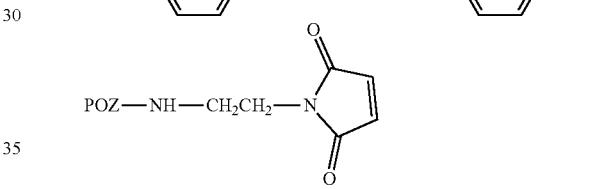

All of the above POZ derivatives react with a group on a target molecule to form a hydrolytically stable linkage between the target molecule and the PO derivative.

Specific POZ Derivatives from Piperidines or Piperazines

As discussed herein, the living POZ cation can be terminated with a substituted or unsubstituted piperidine or piperazine or derivatives of the foregoing. The substitutions include, but are not limited to, those groups described with respect to a substituted alkyl and substituted and unsubstituted alkyl, alkenyl, aralkyl or heterocycloalkyl. These POZ derivatives are difficult to illustrate with the above Schemes 1-4 because the linking group, designated C in Scheme 4, is part of the piperidine or piperazine ring structure. For example, the POZ cation can be trapped with 4-piperidine methanol to yield a POZ alcohol, with 4-piperidine butyric acid to yield a POZ carboxylic acid, or with piperazine itself to yield a POZ amine:

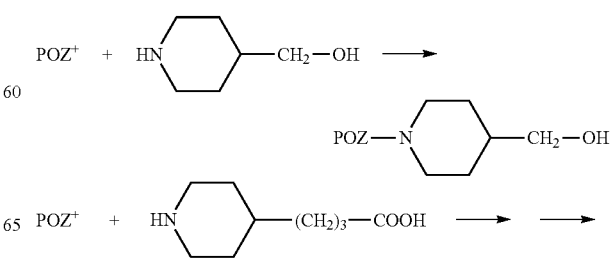

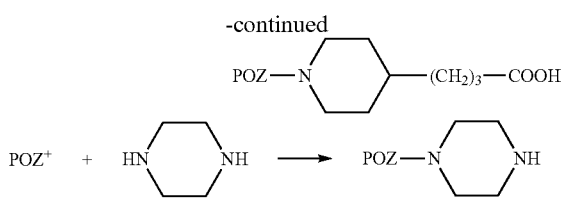

Terminations with such piperidines and piperazines are useful because the strong nitrogen nucleophile gives rapid and clean termination to introduce a terminal active functional group. At least four piperidine and piperazine derivatives are commercially available, including 1-piperazinepropanol, 4-piperidine butyric acid, 3-piperidine carboxylic acid and 4-piperidine methanol, and others could be readily synthesized.

It is to be understood that any of the POZ derivatives described above which are prepared from POZ alcohols, acids or amines could be prepared from such piperidines or piperazines in which the nitrogen-containing ring provides the alcohol, acid or amine. For example, the following compounds can be prepared from the above POZ terminated with 4-piperidine methanol:

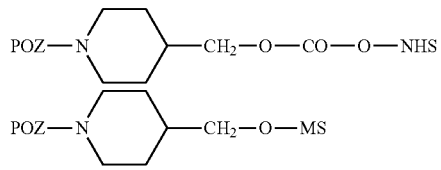

These compounds in turn could be converted to a range of useful derivatives including acetals, maleimides, and active esters:

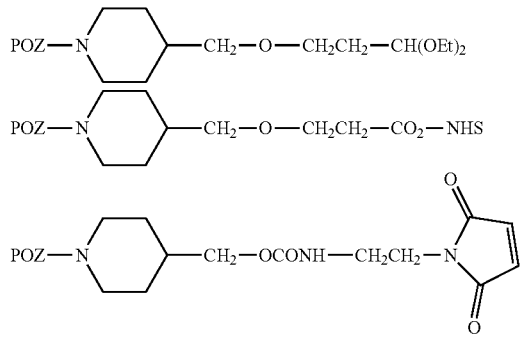

Use of the POZ Derivatives

The described monofunctional POZ derivatives, through the active functional groups, may be used to produce a hydrolytically stable target molecule-POZ conjugate. In addition, using the monofunctional POZ derivatives described herein, in certain embodiments one target molecule is bound by each POZ derivative. The variety of active functional groups present in the monofunctional POZ derivatives allow for the monofunctional POZ derivatives to be coupled to a variety of groups on the target molecule using a variety of reaction chemistries. For example, when the active functional group is an aldehyde, the monofunctional POZ derivative reacts predominately with N-terminal amines of a target protein molecule in a defined pH range. When the active functional group is an active ester, the monofunctional POZ derivative reacts predominately with amines, including, but not limited to, lysine groups on a target molecule. Likewise, when the active functional group is an active carbonate or Cresylate, the monofunctional POZ derivatives react with amines, but with reaction conditions and selectivity different from active esters and aldehyde. Furthermore, when the active functional group is a vinylsulfone, maleimide or iodoacetamide, the monofunctional POZ derivative reacts predominately with thiols, but the reaction conditions differ for each of these groups, providing a range of reaction conditions appropriate for a range of target molecules.

Importantly, each of the monofunctional POZ derivatives formed using the synthetic scheme above is capable of forming hydrolytically stable target molecule-POZ conjugates.

Physiologically active target polypeptide and protein target molecules, also referred to herein as biopharmaceuticals, have played important roles in clinical therapeutics. Some examples of biopharmaceuticals that act in-vivo are the interleukins, granulocyte colony stimulating factor (GCSF), granulocyte/macrophage colony stimulating factor (GMCSF), macrophage colony stimulating factor (MCSF), erythropoietin (EPO), α-, β- and γ-interferons, insulin, growth hormones, somatostatin, vasopressin, modified peptides, animal and microorganism derived peptides and human and animal antibodies and antibody fragments.

In one embodiment, the target molecule is a polypeptide. For example, a monofunctional POZ derivative may be coupled to the therapeutically important protein, such as, but not limited to, GCSF or EPO. One exemplary reaction for forming a POZ-GCSF conjugate is illustrated schematically below by the following reaction:

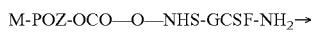

M-POZ-OCO—O—NHS-GCSF-NH$_2$→

M-POZ-OCONH-GCSF

In this embodiment, the amine shown on GCSF represents one of the several available lysine groups.

Similarly GCSF contains an available thiol group, and under the proper conditions a monofunctional POZ derivative with maleimide as the active functional group can react with this thiol group.

POZ derivatives can be coupled to peptides as well. For example, a monofunctional POZ derivative with an active ester as the active functional group can couple to the available amino groups on insulin:

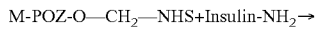

M-POZ-O—CH$_2$—NHS+Insulin-NH$_2$→

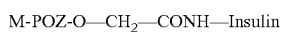

M-POZ-O—CH$_2$—CONH—Insulin

In an alternate embodiment, the target molecule is a small molecule, drug or a diagnostic agent.

The foregoing examples show POZ-target molecule conjugates between the monofunctional POZ derivatives described herein and in U.S. patent application Ser. No. 12/529,001. However, other POZ derivatives may be used in the POZ-target molecule conjugates described herein. In an alternate embodiment the POZ component used in the formation of the POZ-EPO conjugate is a POZ derivative as described in International Patent Application Nos. PCT/US2008/078159, PCT/US2009/030762 or PCT/US2009/050286. Furthermore, the active functional group may be at the initiator end, the terminal end or at a pendent position. Furthermore, the POZ portion of the POZ derivative may be a homopolymer or a random or block copolymer as described in International Patent Application Nos. PCT/US2008/078159, PCT/US2009/030762 or PCT/US2009/050286. The foregoing patent applications are hereby incorporated by reference for such teachings.

Polymer-modified biopharmaceuticals have proven to have great utility in modern clinical therapeutics. These preparations have been shown to have great versatility in the treatment of blood disorders such as anemia and neutropenia, viral infections, growth disorders and autoimmune disorders. However, despite this promise the use of biopharmaceuticals has been noted to have several shortcomings.

First, the bioactivity of many biopharmaceuticals is limited by a short-half life in blood. For example, in order to reach clinically optimal levels, EPO must be injected 2-3 times a week to anemia patients or reticulocyte levels in the blood will fall rapidly. Frequent administration to achieve maximum efficacy is problematic because of poor patient compliance. Bioactivity is limited by rapid metabolism, decomposition by proteolysis and binding to serum albumin. Physical changes (aggregation or denaturation) and chemical changes (oxidation or modification of chemical bonds in general) of the protein molecule can occur under unfavorable storage and exposure conditions. At elevated temperatures (above 8° C.) unfolding of the protein occurs and this leads to a loss in biological activity. Denaturation may lead to aggregation and particulate formation.

Second, side effects have been associated with frequent administration of many biopharmaceuticals. For EPO, such side effects include, but are not limited to, inflammation and infection at the site of administration. Such side effects cause additional health problems for the patient and further contribute to poor patient compliance.

Third, antigenicity has been observed as a recurring side effect associated with a number of natural or recombinant biopharmaceuticals. Antibodies are produced in-vivo and can lead to neutralization of the biopharmaceutical and in some cases also create allergic reactions. In the former instance, higher doses and/or more frequent administration of biopharmaceuticals may circumvent the neutralizing effect of antibodies. However, higher doses may aggravate the observed side effects and results in increases in dosing frequency may result in reduction of patient compliance.

To solve the above mentioned problems, a number of strategies have been employed. Entrapment of the biopharmaceutical in an inert phosphotidylcholine based liposome, vesicle or nanocapsule has been used. The inert carrier will accumulate in the reticuloendothelial system (RES).

In addition, bonding of the biopharmaceutical to a macromolecule or polymer substrate such as albumin, polylysine, hyaluronic acid or polyethylene glycol (PEG) has been used. Covalent modification of proteins increases the protein's effective size and reduces renal clearance (Abuchowski et al., 1984; Hershfield, 1987; Meyers et al., 1991). Polymer conjugation also improves in-vivo stability (protection from proteases), improves protein solubility and lowers antigenicity (Katre et al., 1987; Katre, 1990).

Traditionally these modifications have been made by reacting terminal electrophiles on the polymer with nucleophiles on the protein (non-enzymatically mediated reactions). Conjugation occurs at the α-amino group on the N-terminal amino acid or on the s-amino groups of lysine within the polypeptide chain. These reactions typically give non-specific attachment of the macromolecule or polymer substrate to the biopharmaceutical and may result in significant loss in bioactivity of the biopharmaceutical. In addition, bonding of the biopharmaceutical to a macromolecule or polymer substrate can be accomplished using enzymatically mediated reactions. The latter approach provides the benefit of increased specificity in the conjugation reactions, which may lead in increased activity in vivo.

Because of the success of polymer-modified therapeutics and biopharmaceuticals in general, for example EPO, it is of interest to expand the range of polymers suitable for such applications, especially to provide polymers having properties not possessed by polymers of the prior art. The present disclosure provides methodologies of attaching POZ and/or POZ derivatives, to biopharmaceuticals and the resulting POZ-biopharmaceutical conjugates. In one embodiment, the POZ-biopharmaceutical conjugates are hydrolytically stable. One advantage of POZ is that the hydrophilicity of the polymer can be varied by changing the nature of the $R_7$ group, such as, but not limited to, changing an alkyl group present in the $R_7$ position from methyl to ethyl to propyl; these changes can lead to differences in the PK profile and to greater activity as shown by an increase in the area under the activity curve.

POZ-Erythropoietin Conjugates

The present disclosure also provides for POZ-EPO conjugates. Erythropoietin (EPO) is a naturally formed glycoprotein that is produced in the kidney and which functions as a colony stimulating factor involved with the regulation of red blood cells. Human EPO was first cloned and amino acid sequence reported by Lin et al. (Proc Natl Acad Sci USA 1985 82: 7582-4) and Jacobs K et al. (Nature 313: 806-810 1985) (each of which is incorporated herein by reference for such teaching). Human EPO is a four helix bundle, typical of members of the hematopoietic growth factor family. In contrast to the invariant amino acid sequence, the carbohydrate structures are variable, a feature referred to as micro-heterogeneity. The differences in carbohydrate moieties, in terms of the branching pattern, complexity, size and charge has profound effects on the pharmacokinetics and pharmacodynamics of EPO. The effects of different glycosylation patterns have been well studied (Darling et al 2002 Biochemistry 41: 14524-14531; Stoning et al 1998 Br J Haematol 100: 79-89; Halstenson et al 1991 Clin Pharmacol Ther 50: 702-712; Takeuchi et al 1990 J Biol Chem 265: 12127-12130) (each of which is incorporated herein by reference for such teaching).

EPO acts on precursor cells in the bone marrow to produce mature red blood cells. rh-EPO has been manufactured using recombinant DNA technology through cloning of the EPO gene and expression in Chinese Hamster Ovary (CHO) cells (Lin, U.S. Pat. No. 5,618,698). EPO is available in formulations such as EPOGEN® and PROCRIT® in 1 mL single dose or 2 mL multi-dose injection vials. These products have been successfully used to treat anemia associated with myelosuppression following chemotherapy in cancer patients, chronic renal failure, and in some cases of HIV infected patients on antiviral therapy. EPO has been administered by intravenous, intramuscular and subcutaneous injection. The measurement of reticulocytes in total erythrocytes is an indicator of EPO activity.

The current formulations of EPO have been associated with certain shortcomings, including those discussed above (for example, short half-life, side effect associated with frequent administration and antigenicity).

Several patents have issued on coupling of PEG to EPO (U.S. Pat. Nos. 6,340,742, 6,583,272, 7,074,755, 7,128,913 and applications WO/2002/049673, 2005/0170457, 2004/0082765, 2004/0266690 and 2006/0276634).

The present disclosure provides methodologies of attaching POZ and/or POZ derivatives, to EPO and the resulting POZ-EPO conjugates. In one embodiment, the POZ-EPO conjugates are hydrolytically stable. In one embodiment, the products obtainable according to the present disclosure comprise polyoxazoline derivatives conjugated to EPO. Such POZ-EPO conjugates may be obtained by non-enzymatic reactions or enzymatic mediated reactions as described herein. The conjugates according to the present disclosure have increased residence time in blood, and produce less immunogenic responses compared to the corresponding unconjugated EPO. In addition, the conjugates of the present disclosure have different PK profiles as compared to unconjugated EPO.

Polyoxazolines have side chains that may sterically hinder the attachment of this polymer to buried amino acid residues on large proteins, such as EPO. One would anticipate that the yields of such a conjugation would be low. Furthermore, it is also surprising that the conjugates obtained using sterically hindered POZ polymers and POZ derivatives maintain their biological activities.

Furthermore, the present disclosure provides methodologies that can be applied to the attachment of the POZ derivative to different amino acid residues of EPO (whether natural or synthetic) and to that of EPO variants and mimetics. For example, POZ polymers could be coupled to the N-terminus of EPO (Alanine 1) or lysine 52 of EPO. The amino acid sequence human recombinant EPO is provided in FIG. 3 (SEQ ID NO. 1).

In one embodiment, the POZ component used in the formation of the POZ-EPO conjugate is a POZ derivative as described herein. In an alternate embodiment the POZ component used in the formation of the POZ-EPO conjugate is a POZ derivative as described in International Patent Application Nos. PCT/US2008/078159 PCT/US2009/030762 or PCT/US2009/050286.

EPO used to produce the POZ-EPO conjugates may be either natural, recombinant or synthetically produced EPO; furthermore, polypeptides having EPO activity may also be used, including, but not limited to EPO polypeptide differing by one or more amino acids from human EPO. Furthermore, EPO having different patterns of glycosylation may be used.

The following EPO polypeptides have the same amino acid sequence as recombinant human EPO, but variations in the methods of production provide differing glycosylation patterns. Epoetin alfa and epoetin beta are described in U.S. Pat. Nos. 4,703,008 and 5,955,422. Epoetin alfa and epoetin beta are produced in chinese hamster ovary (CHO) cells. Epoetin alfa is available under the trade names procrit (Ortho Biotech), eprex (Johnson & Johnson), epogin (Chugai) or epogen (Amgen). Epoetin beta is available under the trade name neorecormon or recormon (Hoffmann-La Roche). Epoetin omega described in U.S. Pat. No. 5,688,679 is produced in baby hamster kidney cells (BHK-21). Epoetin omega is available under the trade names epomax (Elanex). Darbepoetin alfa (Amgen) is available under the trade name aransep (Macdougall I C, Kidney Int Suppl. 2002 May; (80):55-61). Darbepoetin alfa was designed to contain five N-linked carbohydrate chains (two more than rhEPO). The amino acid sequence differs from that of rhEPO at five substitutions (Ala30Asn, His32Thr, Pro87Val, Trp88Asn, Pro90Thr), thus allowing for additional oligosaccharide attachment at asparagine residues at position 30 and 88. Each of the references in this paragraph are hereby incorporated by reference for the teaching of the EPO amino acid sequence and methods of production.

In addition, forms of EPO with various point mutations have been described (Elliot et al 1997 Blood 89: 493-502; Elliot et al 1996 Blood 87: 2702-2713; Syed et al 1998 Nature 395: 511-516; O'Narhi et al 2001 Protein Engineering 14: 135-140; Bill et al 1995 Biochimica et Biophysica Acta 1261: 35-43; Yamaguchi et al 1991 J Biol Chem 266: 20434-20439; and US Patent Publication No. 20080194475). Such EPO variants have been reported to have similar properties to native or recombinant EPO. Each of the references in this paragraph are hereby incorporated by reference for the teaching of the EPO amino acid sequence and methods of production.

TGase Catalyzed Conjugate Formation

As discussed above, enzymatically mediated reactions may provide benefits over non-enzymatically mediated reactions.

One example of an enzymatically mediated reaction is based on use of transglutaminase (TGase). TGase, obtained from guinea pig liver or *Streptomyces mobaraensis*, is used in the conjugation process to facilitate the attachment of a polymeric amine to the glutamine residue of a peptide or protein. In this reaction, the enzyme effectively replaces the amine of the glutamine with the amine group from the polymeric amine.

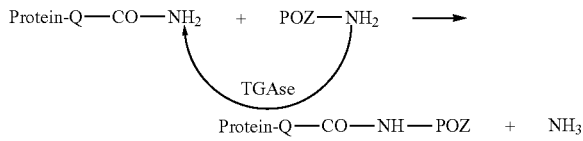

This TGase approach has been used to attach PEG, polylysine and polysaccharides to proteins. The attachment of PEG amine to biopharmaceuticals using TGase has been reported by Fontana et al., *Advanced Drug Delivery Reviews*, 60 (2008) 13-28. U.S. Pat. No. 6,010,871 (January 2000) broadly covers the bonding of polylysine, PEG and monoclonal antibodies to proteins and peptides using TGase. U.S. Patent application 2006/0116322 (June 2006) is for a composition of EPO conjugated with polyalkylene oxide (PEG and propylene glycol) using TGase. A more recent application WO 2008/017603 (February 2008) is for a composition of G-CSF and PEG using TGase. The attachment of polysaccharides such as dextran, carboxymethyl-cellulose and polydextrose to bovine pancreatic trypsin through a transglutaminase-catalysed reaction has been reported by M. Villalonga et al. (World Journal of Microbiology and Biotechnology, 2006). The use of cationic saccharides such as polylysine-dextran in the conjugation on to β-lactoglobulin with the aid of the TGAse enzyme was reported by T. Ikeuchi et al. (Biosci. Biotechnol. Biochem., 2008). In another report, sorghum protein was cross-linked with dextran or galactomannan with the aid of TGAse in order to get a stable complex (E. Babiker and A. Kato, Molecular Nutrition & Food Research).

The present disclosure provides methodologies utilizing the enzyme TGase to attach the biocompatible polymer POZ and POZ derivatives to biopharmaceuticals, such as but not limited to, proteins and polypeptides. As discussed above, one advantage of POZ is that the hydrophilicity of the polymer can be varied by changing the nature of the $R_7$ group, such as, but not limited to, changing an alkyl group present in the $R_7$ position from methyl to ethyl to propyl; these changes can lead to differences in the PK profile and to greater activity as shown by an increase in the area under the activity curve.

A potential concern relating to the producing desired POZ-biopharmaceutical conjugates is that POZ amines may make poor TGase substrates because of steric hindrance resulting from the side chains present in POZ. TGase catalyzes acyl transfer between the γ-carboxyamide group of the glutamine (acyl donor) and the polymeric primary amine (acyl acceptor), and it is reasonable to hypothesize that side chains on the polymer would lead to steric inhibition of the acyl transfer. The inventors of the present disclosure have found that simple POZ amines are quite inefficient at TGase-mediated protein conjugation. The present disclosure reveals that moving the terminal amine group farther from the POZ side chains by use of spacer moieties can lead to a practical process giving efficient coupling of POZ amines to biopharmaceuticals, such as but not limited to, proteins and polypeptides. In one embodiment, the POZ derivative contains an amine group separated from the POZ polymer by a spacer moiety of 3, 4, 5, 6, 7 8, 9 or 10 or more atoms, such as, but not limited to, carbon, oxygen, nitrogen and sulfur atoms.

The structure of the products obtained from this reaction can be represented by the formula:

Polypeptide-CH$_2$CH$_2$—CO—NH-POZ

In this structure the —CH$_2$CH$_2$—CO— group represents a protein glutamine residue.

Specific embodiments of the POZ amines falling under the general formula above include, but are not limited to:

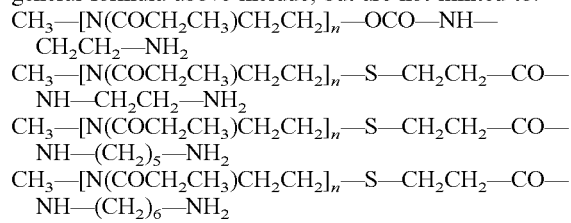

CH$_3$—[N(COCH$_2$CH$_3$)CH$_2$CH$_2$]$_n$—OCO—NH—CH$_2$CH$_2$—NH$_2$

CH$_3$—[N(COCH$_2$CH$_3$)CH$_2$CH$_2$]$_n$—S—CH$_2$CH$_2$—CO—NH—CH$_2$CH$_2$—NH$_2$

CH$_3$—[N(COCH$_2$CH$_3$)CH$_2$CH$_2$]$_n$—S—CH$_2$CH$_2$—CO—NH—(CH$_2$)$_5$—NH$_2$

CH$_3$—[N(COCH$_2$CH$_3$)CH$_2$CH$_2$]$_n$—S—CH$_2$CH$_2$—CO—NH—(CH$_2$)$_6$—NH$_2$

As discussed herein, the nature of the group at R$_7$ and the initiator position can be varied, with ethyl and methyl being used for exemplary purposes only POZ-Lipid Conjugates The present disclosure also provides for POZ-lipid conjugates. POZ-lipid conjugates of the present disclosure comprise a lipid portion linked to a polyoxazoline portion; the polyoxazoline portion may be any such polyoxazoline polymer of derivative described or referenced herein. In one embodiment, the lipid portion comprises at least one hydrophobic moiety and a chemical group capable of forming a linkage with a chemical group on the polyoxazoline portion. In an alternate embodiment, the lipid portion comprises two hydrophobic moieties and the chemical group is located at the head group position and the polyoxazoline portion is linked to the lipid portion through the chemical group located at head group position.

Lipids are a class of molecules that contain a hydrophobic portion and a hydrophilic portion. The hydrophobic and hydrophilic portions provide an amphipathic property to these molecules allowing them to aggregate in a specific manner to form bilayers and vesicles/liposomes in aqueous environments. Phospholipids are a type of lipids that have such amphipathic character. The head group of a phospholipid is hydrophilic whereas the tail groups are hydrophobic. The hydrophilic head group contains the negatively charged phosphate group, and may contain other polar groups. The hydrophobic tail group generally comprises long fatty acid hydrocarbon chains. When placed in an aqueous environment, phospholipids form a variety of structures depending on the specific properties of the phospholipid.

The lipid portion of the polyoxazoline-lipid conjugates may comprise any lipid capable of forming a vesicle/liposome, either alone or in combination with other lipid components of the liposomal compositions (described below). The lipids may be synthetic or naturally occurring. Regardless of the exact nature of the lipid comprising the lipid portion, the lipid contains a chemical group that is suitable for forming a linkage with a chemical group on the polyoxazoline portion. The nature of the linkage will depend on the chemical group present on the polyoxazoline portion and the chemical group present on the lipid portion. In one embodiment, the chemical group that forms the linkage with the polyoxazoline portion is located in the head group of the lipid portion. For example, the chemical group may be an amine group, hydroxyl group, aldehyde group or a carboxylic acid group; other chemical groups are not excluded. The polyoxazoline portion may be conjugated via appropriate chemical group on the initiator or the terminal end of the polymer.

In general the covalent attachment of polymers to a vesicle-forming lipid is accomplished by reaction of an active chemical group on the polyoxazoline portion with a complementary chemical group on the lipid portion. The chemical groups on the polyoxazoline portion and/or the lipid portion may be activated prior to the reaction (such as, but not limited to, removal of any protecting groups). A hydroxyl, amine or carboxyl group may be activated for coupling by monofunctional activating agents, such as N-hydroxysuccinimide, ethylchloroformate, DCCD, Woodward's Reagent K, cyanuric acid and trifluoromethanesulfonyl chloride among others. A number of bifunctional crosslinking reagents containing groups with different reactivities, such as some diisocyanates, may also be used.

The hydrophobic moieties are typically acyl chains containing an alkyl portion. The alkyl portion of the acyl chain may vary in length; in addition the alkyl portion may be saturated (contain no double bonds) or contain one or more areas of unsaturation (contain one or more double bonds). When unsaturated, the alkyl portion may have varying degrees of unsaturation, for example, from 1 to 4 areas of unsaturation. When the alkyl portion contains an area of unsaturation, the hydrogen atoms at the double bond may be in the cis or trans configuration. In one embodiment, the alkyl portion of the acyl chains contains from 14 to 24 carbons. When the lipid portion contains two hydrophobic moieties, the alkyl portions of the two hydrophobic moieties may be the same or may be different.

Exemplary lipids, POZ-lipid conjugates, methods of synthesizing the same and methods of using the foregoing are described in International Application No. PCT/US09/50286, which is hereby incorporated by reference for such teachings.

Liposomal Compositions

The present disclosure also provides for liposomal compositions. The Liposomal compositions of the present disclosure incorporate a polyoxazoline-lipid conjugates of the present disclosure and provide a number of advantages over liposomal compositions of the prior art. For example, the liposomal compositions of the present disclosure provide a longer residence time for the liposomal composition in the body; as such the liposomal compositions can release entrapped target molecules, such as a therapeutic agent, over a longer period of time. In addition, prolonged residence times allow the liposomal composition to effectively reach various sites in the body and enter such regions.

The polyoxazoline-lipid conjugate of the present disclosure is used in preparing a liposomal composition. In one embodiment, the liposomal composition contains a therapeutic agent for the treatment of human disease. In an alternate embodiment, the liposomal composition contains a diagnostic agent. In still a further embodiment, the liposomal composition contains a targeting agent to target the liposomal composition to a particular cell or tissue. Liposomal compositions of the present disclosure may also contain combinations of the foregoing (for example, a therapeutic agent and a targeting reagent or a diagnostic agent and a targeting agent). In one embodiment the polyoxazoline-lipid conjugate when incorporated in a liposomal composition is present at a mole ratio of about 0.5% to about 50% mole percent in the lipid layer of the liposomal composition, at a mole ratio of about 1% to about 30% mole percent in the lipid layer of the liposomal composition, at a mole ratio of about 2% to about 20% mole percent in the lipid layer of the liposomal composition or at a mole ratio of about 5% to about 10% mole percent in the lipid layer of the liposomal composition. In such embodiment, the polyoxazoline-lipid conjugate may form a layer which is effective to extend the blood circulation time of the liposomes over that of the liposomes lacking the polyoxazoline-lipid conjugate.

The liposomal composition comprises a polyoxazoline-lipid conjugate of the present disclosure in combination with other lipid components (lacking polyoxazoline components) that are capable of forming vesicles and/or liposomes (the lipid components lacking a polyoxazoline component are referred to as underivatized lipids). The underivatized lipids include any amphipathic lipids having hydrophobic and polar head group moieties, and which (a) can form spontaneously into bilayer vesicles in water or (b) are stably incorporated into lipid bilayers, with its hydrophobic moiety in contact with the interior, hydrophobic region of the bilayer membrane, and its polar head group moiety oriented toward the exterior, polar surface of the membrane.

Exemplary liposomal compositions containing POZ-lipid conjugates, methods of synthesizing the same and methods of using the foregoing are described in International Application No. PCT/US09/50286, which is hereby incorporated by reference for such teachings.

Target Molecule-POZ Conjugates

The present disclosure describes a variety of monofunctional POZ derivatives capable of forming a linkage with a target molecule to produce a hydrolytically stable target molecule-POZ conjugate as discussed above. In a general embodiment, the present disclosure provides for a hydrolytically stable target molecule-POZ conjugate having the general formula (IV):

A-B-TM (IV)

Wherein,
A is a monofunctional POZ derivative described herein, minus any leaving groups eliminated during the reaction of the active functional group on the POZ derivative with a binding partner on the target molecule;
TM is a target molecule; and
B is a hydrolytically stable linkage formed between the active functional groups of a monofunctional POZ derivative of the present disclosure and a binding partner on the target molecule, it being understood that the nature of the hydrolytically stable B linkage will depend on the nature of the active functional group on the monofunctional POZ derivative and the binding partner on the target molecule. Exemplary active functional groups, binding partners and B linkages are provided in Table 3 below. The listing in Table 3 is not meant to be exhaustive and other combinations and resulting B linkages may be envisioned given the teachings of the present disclosure.

As discussed above, the POZ component used in the formation of the POZ-target molecule conjugate is a POZ derivative as described in International Patent Application Nos. PCT/US2008/078159, PCT/US2009/030762 or PCT/US2009/050286.

TABLE 3

| Active functional group | Binding Partner on target Molecule | B linkage |
| --- | --- | --- |
| Tresylate | SH | Thioether (—S—) |
| Maleimide | SH | Thioether (—S—) |
| Active carbonate | $NH_2$ | Urethane (—NH—CO—O—) |
| Active ester | $NH_2$ | Amide (—NH—CO—) |
| Aldehyde | $NH_2$ (amine) | Amine (—NH—) |

GENERAL EXAMPLES

Examples 1-36 of U.S. patent application Ser. No. 12/529,001 are hereby incorporated by reference.

Materials and General Methods

Reagents were purchased from EM Science, Acros Organics, ABCR or Aldrich. Dry solvents were prepared by distillation followed by drying by distillation over calcium hydride. Monomers were distilled over calcium hydride or freeze-dried using dry benzene. GPC was performed on an Agilent Technologies instrument with an RI detector. Two Phenogel GPC columns (Phenomenex, 5 microns, 300×7.8 mm) were used in series at 60° C.). The mobile phase was DMF. A calibration curve was generated with M-PEOZ-OH samples of different molecular weights as determined by MALDI TOF. MALDI-TOF MS was performed with a Bruker Microflex with dithranol matrix. The samples were prepared by mixing chloroform solutions of the polymer and matrix (10 mg/mL) in a ratio of 1:1 (v/v). NMR spectra were recorded in $CDCl_3$ on a Varian 500 MHz instrument.

Example 1. Preparation of 20 kDa H-PEOZ-Hydrazide

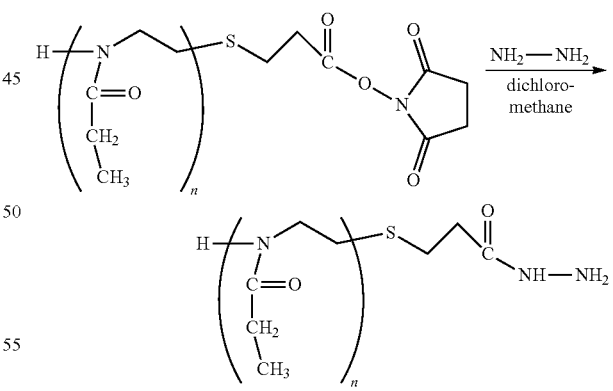

The synthesis of 20 kDa polyoxazoline succinimidyl thiopropionate has been described (H-PEOZ-T-SPA 20 K, GFC shows 83% of —O—Su; GPC showed a Mn=18,243 Da, PDI=1.055, Mp=19,973 Da; and MALDI-TOF showed a Mn=20,972 Da). Hydrazine monohydrate, $NH_2NH_2 \cdot H_2O$, 98% was from Aldrich, FW 50.06, d 1.032.

H-PEOZ-T-SPA 20 K (2.0 gm, $9.1240 \times 10^{-5}$ mol, 1 equiv.) was first dissolved in anhydrous dichloromethane (90 mL) and this solution was transferred into an addition funnel. In a 250 mL round bottom flask, hydrazine monohydrate (452 µL, $9.1240 \times 10^{-3}$ mol, 100 equiv.) was dissolved in anhydrous dichloromethane (5 mL). Under an argon atmosphere, the H-PEOZ-T-SPA solution in dichloromethane was added to the hydrazine solution drop wise over one hour with rapid stirring. This solution was stirred overnight at ambient temperature and in an argon atmosphere. The white precipitate that was formed in the reaction mixture was filtered out and the filtrate was collected and concentrated to near dryness on a rotary evaporator. The remaining highly concentrated solution was further dried under vacuum for one hour. The residual solid was next dissolved in deionized water (40 mL) and sodium chloride (6 gm) was added to the solution. The pH of the solution was adjusted to 3.0 by the slow addition of 1.0 N HCl acid. This solution was next extracted three times with dichloromethane (50 mL each time). The collected dichloromethane pool was dried over anhydrous sodium sulfate, filtered, and concentrated with a rotary evaporator and then precipitated in ethyl ether. The precipitated solid was recovered by filtration, and was dried under vacuum. Yield: 1.8 gm. HPLC analysis showed a 97% of substitution of H-PEOZ-Hydrazide (data not shown).

Example 2. Conjugation of Heparin by 20 kDa H-PEOZ-Hydrazide Through Carbohydrate Reducing Terminus A 50 mg/mL solution of 20 kDa H-PEOZ-Hydrazide2 (2,222 µL, $5.5556 \times 10^{-6}$ mole, 5 equiv.) was added to heparin sodium salt (Grade I-A, purchased from Sigma-Aldrich, MW 17000–19000 Da, 20 mg, $1.1111 \times 10^{-6}$ mole, 1 equiv.) in pH 3.0 acetic acid solution. The solution was allowed to stir at room temperature for 10 minutes. The solution pH was adjusted to 3.0 by adding 0.1 N HCl acid. To this solution, freshly prepared 1 M $NaBH_3CN$ in deionized water (111.1 µL, $1.1111 \times 10^{-4}$ mole, 100 equiv) was added. The solution was stirred at room temperature for 10 minutes, and then incubated at 37° C. for overnight. The reaction mixture was analyzed by GFC using a BioSEP-SEC-S 4000 column. GFC showed the formation of H-PEOZ-heparin conjugate (data not shown).

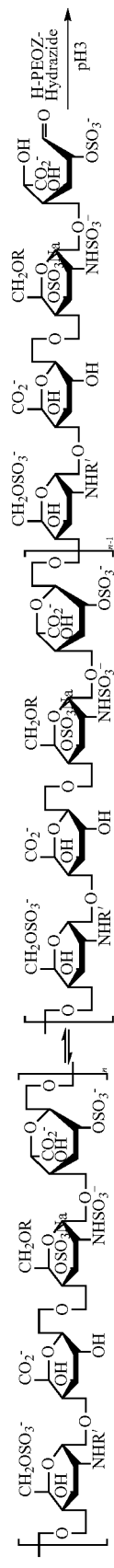
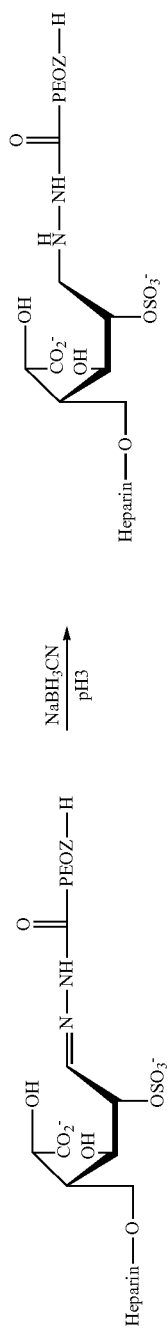

Example 3. Conjugation of Dynorphin A (1-13) at C-Terminus by 5 kDa M-PEOZ-Hydrazide Using EDC as Coupling Agent

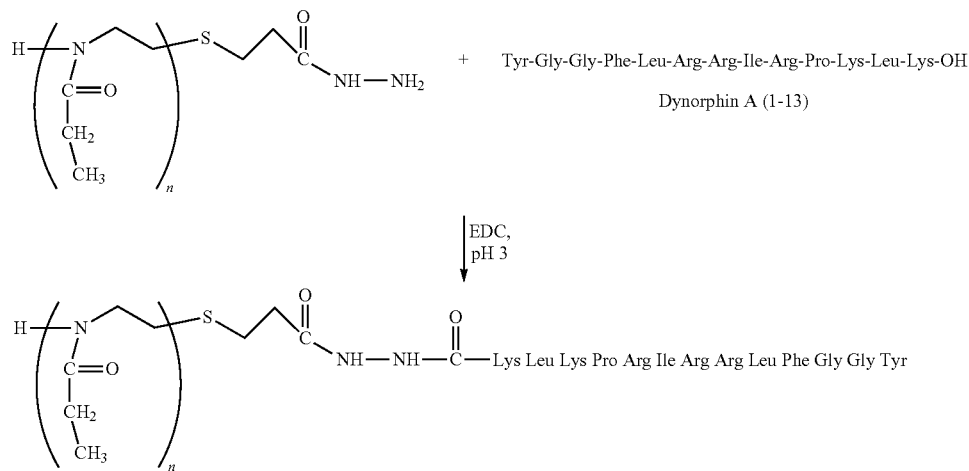

Dynorphin A (dynorphin 1-13) (Bachem, 0.55 mg, $2.2133 \times 10^{-7}$ mol, 1 equiv.) was dissolved in 250 µL of 50 mM 2-(N-morpholino)ethanesulfonic acid (MES) buffer at pH 3.0. A 109.5 µL aliquot of 50 mg/mL 5 kDa M-PEOZ-Hydrazide 5K (5.5 mg, $1.1066 \times 10^{-6}$ mol, 5 equiv) in 50 mM MES buffer at pH 3.0 was prepared and filtered through a 0.2 µm syringe filter. This 5 kDa M-PEOZ-Hydrazide solution was then added to the dynorphin A solution. The solution pH was adjusted to 3.0 by drop by drop addition of a 50 mM HCl acid solution. A solution of N-(3-Dimethylaminopropyl)-N'-ethyl-carbodiimide hydrochloride (EDC, purchased from Fluka) in deionized water (31 µL, 100 mg/mL, $1.6097 \times 10^{-5}$ mol, 20 equiv.) was added into the mixture. The solution pH was adjusted to 3.0 by slowly adding 50 mM HCl. The solution was allowed to stir at room temperature for 3 hours. The reaction mixture was analyzed by SDS-PAGE, which confirmed the formation of mono-PEOZ-Dynorphin A conjugate. The reaction mixture of 5 kDa M-PEOZ-Hydrazide and Dynorphin A (1-13) was analyzed by SDS-PAGE using an XCell SureLock Mini-Cell Electrophoresis System. A 4-12% NuPAGE Bis-Tris Mini Gel was used with 1×MES SDS Running Buffer. The electrophoresis was done for 35 minutes with constant voltage at 200 V. The reaction mixture (10 µL) was pre-mixed with 10 pL NuPAGE LDS Sample Buffer (4×) and 20 µL of deionized water. The gel was stained by GelCode Blue Stain, and de-stained. Lane 1: Mark 12 unstained protein standard. 10 µL. Lane 2: M-PEOZ-Dynorphin A conjugation mixture after 3 hours of reaction, 10 µL loading.

The POZ 5 K conjugate showed in-vitro µ-, δ-, κ-opioid binding activity similar to that of unconjugated dynorphin A (1-13).

Example 4. Conjugation of Lysozyme at Carboxylate Groups by 5 kDa M-PEOZ-Hydrazide Using EDC as Coupling Agent

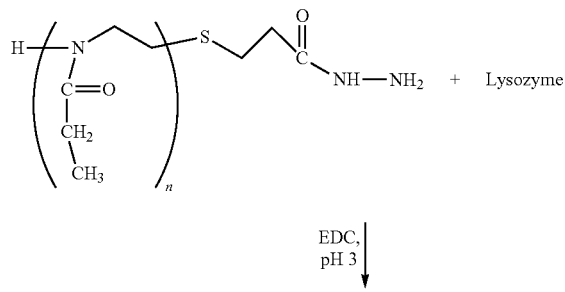

-continued

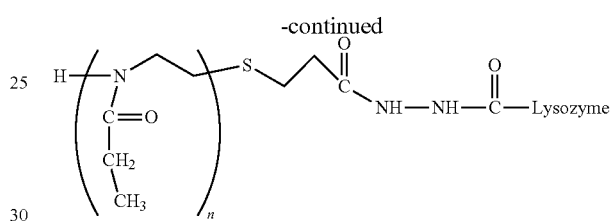

Lysozyme (from chicken egg white, MW 14,307 Da, purchased from Sigma-Aldrich, 26 mg, $1.63995 \times 10^{-6}$ mol, 1 equiv.) was dissolved in 1 mL of 50 mM (2-(N-morpholino) ethanesulfonic acid (MES) buffer at pH 3.0. An aliquot of 50 mg/mL 5 kDa M-PEOZ-Hydrazide (Mn 4,952 Da, 812 µL, $8.1998 \times 10^{-6}$ mol, 5 equiv) in 50 mM MES buffer at pH 3.0 was prepared and filtered through a 0.2 µm syringe filter. The 5 kDa M-PEOZ-Hydrazide solution was added to the lysozyme solution. The solution pH was adjusted to 3.0 by addition of 0.1 N HCl. An aliquot of a freshly prepared 100 mg/mL solution of N-(3-Dimethylaminopropyl)-N'-ethyl-carbodiimide hydrochloride (EDC, purchased from Fluka) in DI water (64 µL, $3.2799 \times 10^{-5}$ mol, 20 equiv.) was added into the mixture. The solution pH was adjusted to 3.0 by addition of 0.1 N HCl. The solution was allowed to stir at room temperature for 1 hour, and then kept frozen at −20° C. The solution was analyzed by reversed phase HPLC and SDS-PAGE. Both reversed phase HPLC and SDS-PAGE continued the formation of mono-, di-, tri- and quad- 5 kDa PEOZ-Lysozyme conjugates. Reversed phase HPLC was performed with a Waters Symmetry SB300 C4 Column using a mobile phase of 0.1% TFA in water (A) and 0.1% TFA in ACN (B). A linear gradient of mobile phases were used during run. Flow rate at 0.5 mL/min; UV at 280 nm.

Example 5. Synthesis of H-PEOZ-O—NH$_2$ 5 kDa a. Synthesis of 5 kDa H-PEOZ-O—NH(Boc)

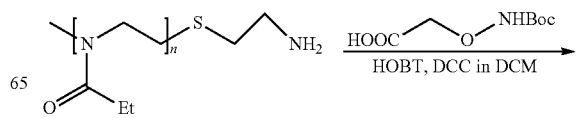

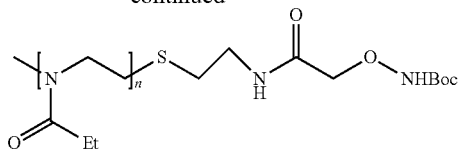

Hydroxybenzotriazole (HOBT, 0.0655 g, 0.485 mmoles) was dissolved in 10 mL of acetonitrile and dried by azeotropic evaporation using a rotary evaporator. Boc-aminooxy acetic acid (0.0445 g, 0.233 mmoles) was added and the mixture was dissolved in 10 mL of dichloromethane. Dicyclohexylcarbodiimide (DCC) (0.060 g, 0.291 mmoles) was added as a solid and the mixture was stirred at room temperature for 2 hours. H-PEOZ-thioamine ($M_n$=5,150 Da, 1.0 g, 0.194 mmoles) was added and the mixing was continued overnight. The next day the mixture was filtered using a 0.2 μm syringe filter and precipitated by slow addition into diethyl ether. The supernatant ether layer was decanted and the residue was collected and dried. The resulting white powder was dried under vacuum to give 1.02 g of the desired compound with a yield of 99%.

$^1$H NMR (Varian, 500 MHz, 10 mg/mL $CDCl_3$) spectrum showed the usual backbone peaks at 1.12 ppm (m, 3H, $CH_3CH_2CO$—); 2.31 ppm (m) and 2.41 s (total area 2H, $CH_3CH_2CO$—); and 3.46 ppm (m, 4H, —$NCH_2CH_2N$—). The terminal group peaks appear at 1.48 ppm (s, 9H, —$CH_2ONHBoc$), 2.73 ppm (m, 4H, —$CH_2SCH_2CH_2NHBoc$), and 4.32 ppm (br s, 2H, —$CH_2ONHBoc$).

b. Synthesis of 5 kDa H-PEOZ-O—$NH_2$

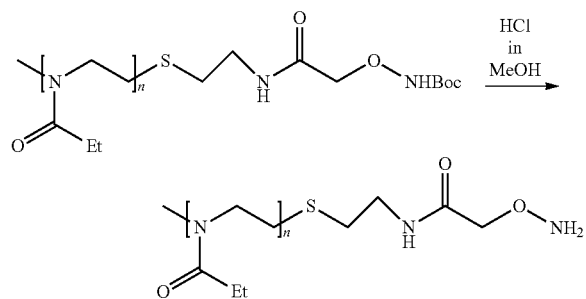

H-PEOZ-O—NH-Boc (1.02 g, 0.192 mmoles) was dissolved in methanolic HCl (3N in MeOH, 20 mL) and stirred for 40 min at room temperature. The mixture was concentrated and dried using a rotary evaporator. The residue was dissolved in dichloromethane and precipitated by slow addition into diethyl ether. The supernatant ether layer was decanted and the residue was collected and dried. The resulting white powder was dried under vacuum to give 1.00 g of the desired compound with a yield of ~100%.

$^1$H NMR (Varian, 500 MHz, 10 mg/mL $CDCl_3$) spectrum showed the usual backbone peaks at 1.14 ppm (m, 3H, $CH_3CH_2CO$—); 2.32 ppm (m) and 2.41 s (total area 2H, $CH_3CH_2CO$—); and 3.47 ppm (m, 4H, —$NCH_2CH_2N$—). The terminal group peak was found at 2.72 ppm (m, 4H, —$CH_2SCH_2CH_2NH$—), 4.16 ppm (m, 2H, —$SCH_2CH_2NH$—CO—$CH_2$—$ONH_2$). The deprotection of Boc group was also confirmed by the disappearance of the peak at 1.48 ppm (s, 9H, —$CH_2ONHBoc$). GPC gave Mp 5182 Da and PD of 1.06.

The aminooxy end group was characterized via derivatization with 4-methoxy benzaldehyde. H-PEOZ-$ONH_2$ (0.0688 g, 0.0133 mmoles), was reacted overnight with 4-methoxy benzaldehyde (32.0 0.263 mmoles) in 5 mL of 0.1 M acetate buffer (counterion sodium, pH 3.6). The mixture was extracted using dichloromethane, concentrated using a rotary evaporator, and precipitated by slow addition into diethyl ether. The supernatant ether layer was decanted and the residue was collected and dried. The resulting white powder was dried under vacuum to give 0.070 g of the desired compound with a yield of ~100%.

$^1$H NMR (Varian, 500 MHz, 10 mg/mL $CDCl_3$) spectrum showed the usual backbone peaks at 1.14 ppm (m, 3H, $CH_3CH_2CO$—); 2.32 ppm (m) and 2.41 (s) (total area 2H, $CH_3CH_2CO$—); and 3.47 ppm (m, 4H, —$NCH_2CH_2N$—). The derivatized terminal group peaks were found at 2.67 ppm (m, 4H, —$CH_2SCH_2CH_2NH$—), 3.79 ppm (s, 3H, —Ar—$OCH_3$), 4.42 ppm (m, 2H, —$SCH_2CH_2NH$—CO—$CH_2$—O—), 6.86 ppm (d, 2H, aromatic), 7.48 ppm (m, 2H, aromatic), 8.11 ppm (d, 1H, —ON═CH—Ar).

Example 6. Coupling of H—PEOZ-T-$NH_2$ (1%) to Hyaluronic Acid (HA)

Sodium hyaluronate (HA, Mw 6×10$^5$, 100 mg, 0.167 mop and H-PEOZ-T-$NH_2$ (Mn 4,381 Da, 11.1 mg, 2.54 μmol) were dissolved in 50 mM 2-(N-morpholino)ethanesulfonic acid (MES) buffer (7 mL) and the pH was adjusted to 4.5-5.0. After addition of 1-ethyl-3-(3-dimethylaminopropyl) carbodiimide hydrochloride (EDC, 2.4 mg, 12.7 μmol), the solution was stirred for 3 hours at room temperature. The reaction was stopped by the addition of 1 M HCl solution and the pH was adjusted to 2.0. The solution was stirred for another 30 minutes. The aqueous solution was then washed with dichloromethane (3×10 mL) to remove any unreacted H-PEOZ-T-$NH_2$. The resulting aqueous solution was lyophilized to collect a white powder.

The degree of PEOZ conjugated to HA is verified by $^1$H-NMR. It was determined that 1.03% of the available carboxylic acids were coupled with PEOZ. This was done by comparing relative integrations of the NMR peaks of —$NHCOCH_3$ on HA and —$COCH_2CH_3$ on PEOZ backbone.

Example 7. Preparation of 5 kDa M-PEOZ-ethylenediamine

M-PEOZ-p-nitrophenylchloroformate 5 kDa was prepared as per procedures previously described, and dissolved in dry chloroform. Ethylenediamine was added and pH adjusted to approximately 8.0 with N-ethyldiisopropylamine (DEAP). The mixture was maintained at room-temperature overnight, and then purified by repeated extractions with a $KHSO_4$ buffer. The organic layer was separated, dried with anhydrous $Na_2SO_4$ and concentrated under vacuo. Ethyl ether was added and the resulting precipitate was collected by filtration and then dried. The content of amine-terminated side chains was determined by Snyder assay and $^1$H-NMR.

Example 8. Conjugation of 5 kDa M-PEOZ-ethylenediamine to GCSF Catalyzed by TGAse The conjugation of POZ-amines to the glutamine residues on a protein is catalyzed by the enzyme transglutaminase (TGAse).

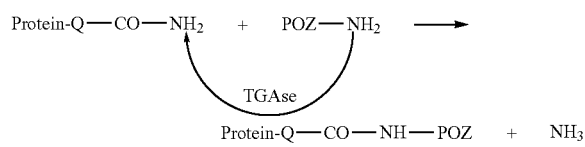

A solution containing granulocyte colony stimulating factor (GCSF, 1.5 mg/mL) in 10 mM phosphate buffer pH 7.0 and M-PEOZ-NH$_2$ (5 kDa) at 10 fold molar excess with respect to the protein, was prepared. After complete dissolution of the polymer and the protein, TGAse was added at an enzyme to substrate ratio (E/S) of 1:75 by weight and the reaction mixture was incubated at room temperature for 4 h.

In order to compare the reaction rates, PEG-NH$_2$ (5 kDa) was conjugated to GCSF using the same reaction conditions as above.

Under the conditions described, there was no completion of conjugation between G-CSF and PEOZ-NH$_2$, while conjugation between PEG and G-CSF was partially complete. Addition of 2 mg of TGAse enzyme to the reaction mixture catalyzed the conjugation process and allowed for the formation of POZ-GCSF. Maldi-TOF mass analysis confirmed the product to have a molecular weight of 23.04 kDa corresponding to the molecular weight of a monoconjugated POZ-GCSF.

The results above show that the rate of conjugation of GCSF with POZ is slower than conjugation of GCSF with PEG. While not being limited by alternate explanations, it is possible the slower reaction rate is attributable to steric hindrance from the adjacent side chains present on the POZ backbone.

Example 9. Preparation of 10 kDa PEOZ-Ethylenediamine and PEOZ-Cadaverine

Conjugation of PEOZ-SPA (NHS) to Ethylenediamine

After dissolution of ethylenediamine in 10 mL of anhydrous dichloromethane, previously prepared 10 kDa PEOZ-succimidyl propionate (SPA, an NHS ester) was added in small increments and the reaction mixture was then allowed to stir for 18 h. After washing with 0.1 N HCl in order to remove any low molecular weight compounds, the organic phase was separated and dried with anhydrous sodium sulfate, and then concentrated under vacuo. The residue was redissolved in water and dialyzed against water for 2 days. The content of amine-terminated side chains was verified by Snyder assay and $^1$H-NMR.

Conjugation of PEOZ-SPA (NHS) to Cadaverine

The linkage of a longer amine spacer to PEOZ-COOH was carried out under the same conditions reported for the conjugation to ethylendiamine.

Example 10. Conjugation of 10 kDa PEOZ-Ethylenediamine and 10 kDa PEOZ-Cadaverine to GCSF Catalyzed by TGAse To a solution containing GCSF (1.5 mg/mL) in 10 mM phosphate buffer pH 7.0, 10 kDa PEOZ-ethylenediamine (PEOZ-Et) or 10 kDa PEOZ-cadaverine (PEOZ-Cad) at 10 fold molar excess with respect to the protein, was added. TGAse was added at an enzyme to substrate ratio (E/S) of 1:75 by weight and the reaction mixtures were incubated at room temperature for 4 h. The reactions were monitored by RP-HPLC using a Zorbax C$_{18}$ column (4.6×250 mm; Agilent, USA) and eluting with a linear gradient of 40-70% acetonitrile containing 0.05% TFA and over a 25 min run time, followed by an isocratic wash at 80% acetonitrile containing 0.05% TFA. The effluent from the column was monitored by measuring the absorbance at 280 nm. For the PEOZ-Et, conjugate yield was 30% or less (data not shown). For PEOZ-Cad conjugate yield was essentially complete at 98% (98% of conjugate, less than 2% of native protein) (data not shown).

The reaction mixture was purified by ion exchange chromatography using an analytical strong-cation exchange column (Tosoh-Haas, SP-SPW, 7.5 mm×7.5 cm). The column was pre-equilibrated with 10 mM phosphate buffer pH 4.7 at a flow rate of 1 mL/min and the protein conjugate was eluted with a NaCl gradient (0.01 to 0.1 M) over 90 min. The product eluent fraction (monitored by the UV absorbance at 280 nm) was collected, dialyzed against 10 mM acetate buffer pH 4.0 to remove any low molecular weight impurities and stored at 4° C. Identification of the reaction mixtures and the final purified products was verified by SDS gel electrophoresis.

Example 11. Conjugation of 20 kDa PEOZ-ethylenediamine and 20 kDa PEOZ-cadaverine to G-CSF Catalyzed by TGAse 20 kDa PEOZ-ethylenediamine (PEOZ-Et) and 20 kDa PEOZ-cadaverine (PEOZ-Cad) were prepared starting from 20 kDa PEOZ-SPA (NHS) under the same conditions reported in Example 9. The obtained amine polymers without further purification were linked to GCSF by TGase catalysis. The reaction was carried out under the same conditions as reported above in Example 10.

Example 12. Conjugation of 20 kDa PEOZ-Hexylamine to GCSF Catalyzed by TGAse 20 kDa PEOZ-hexylamine was prepared starting from 20 kDa PEOZ-SPA (NHS) under the same conditions reported above for the preparation of 1-kDa PEOZ-NH$_2$. To a solution of GCSF (12.6 mg, 1 equiv.) in 2 mL was added a 50 mg/mL solution of H-PEOZ-Hex-NH$_2$ (MW 20 kDa, 5 equiv.) in 10 mM sodium phosphate buffer at pH 7.0, followed by addition of TGAse (33.6 mg of Activa RM contains 1 wt % Transglutaminase, obtained from Ajinomoto Food Ingredient LLC). The reaction mixture was allowed to shake gently at room temperature for 5 hours, and then acidified to 4.0 with 1N HCl. The crude mixture was analyzed by SEC-HPLC using a Phenomenex BioSEP SEC 53000 column, and monitored at 280 nm. The mobile phase contained 50 mM sodium phosphate buffer at pH 6.4 with 5 v/v % ethanol. SEC-HPLC showed about 65% of PEOZ conjugation, predominantly mono-conjugated species (data not shown).

The solution was loaded onto a 60.5 mL SP Sepharose HP 26/114 column (media from GE Healthcare and packed in-house) pre-equilibrated with 20 mM sodium acetate buffer at pH 4.0. Bound proteins were step eluted with 20 mM sodium acetate buffer at pH 4.0, 1 M NaCl. Fractions containing the 20 kDa H-PEOZ-Hex-GCSF were pooled, concentrated, and buffer exchanged into 10 mM sodium acetate buffer at pH 4.0 with 0.004 v/v % Tween 20 by ultrafiltration in an Amicon Stirred Ultrafiltration Cell. The conjugate was analyzed by SEC-HPLC, which showed that H-PEOZ-20K-Hex-GCSF conjugate was free from native G-CSF and di-PEOZ-G-CSF.

Example 13. Conjugation of 10 kDa and 20 kDa PEOZ-Aldehyde at the N-Terminus of GCSF by Reductive Amination A solution of 62.94 mg/mL H-PEOZ-Propionaldehyde (1.8 mL, 10 equiv. for MW 20 kDa) in 1 mM HCl was added into GCSF solution (1.0 equiv of 0.6 mg/mL in sorbital, Tween 20, and acetate buffer). The solution pH was 4.6. Following five minutes of shaking at room temperature, a freshly prepared solution of sodium cyanoborohydride (NaBH$_3$CN) in deionized water (200 µL, 850 mM) was added to the mixture. The solution was allowed to shake gently at 4° C. for 21 hours. The solution pH was adjusted to 4.0 by 0.1 N HCl. The crude reaction mixture was analyzed by SEC-HPLC using a Phenomenex BioSEP SEC 53000 column, and monitored at 280 nm. The SEC-HPLC showed 51% PEOZ conjugation.

The mixture was purified on a 60 mL SP Sepharose HP column (media purchased from GE Healthcare; the column was packed in-house) pre-equilibrated with 20 mM sodium acetate buffer at pH 4.0. Bound proteins were step eluted with 20 mM sodium acetate buffer at pH 4.0 containing 1 M NaCl. Fractions containing the H-PEOZ-N$^{ter}$-GCSF were pooled, concentrated, and buffer exchanged into 10 mM sodium acetate buffer at pH 4.0 with 0.004 v/v % Tween 20 by ultrafiltration in an Amicon™ Stirred Ultrafiltration Cell (Millipore, Model 8050, 50 mL) using a regenerated cellulose membrane (Millipore, YM10, Dia. 44.5 mm, NMWL 10,000). The purity of purified H-PEOZ-20 K-N$^{ter}$-GCSF was analyzed by SEC-HPLC and shows the conjugate consisted of >99% of mono H-PEOZ-N$^{ter}$-G-CSF. The results were confirmed by and SDS-PAGE (data not shown).

The results of the conjugation yield from examples 10, 11, 12 and 13 are summarized in Table 4 below.

TABLE 4

Degree of PEOZ-GCSF conjugation

| Conjugates | Conjugation degree (%) | Amount of native protein (%) |
| --- | --- | --- |
| 20 kDa M-PEOZ-Et-GCSF | 20 | 80 |
| 20 kDa M-PEOZ-Cad-GCSF | 95 | 5 |
| 20 kDa H-PEOZ-Hex-GCSF | 65-75* | 25-35* |
| 20 kDa H-PEOZ-N$^{ter}$-GCSF | 51 | 49 |
| 10 kDa M-PEOZ-Et-GCSF | 30 | 70 |
| 10 kDa M-PEOZ-Cad-GCSF | 98 | 2 |
| 10 kDa H-PEOZ-N$^{ter}$-GCSF | 49 | 51 |

*range from different batches prepared on different scales.

The results above show that the longer NH$_2$ spacer on the PEOZ allows for a more complete conjugation. PEOZ-Et-NH$_2$ was less reactive than either PEOZ-Cad-NH, or PEOZ-Hex-NH$_2$ with respect to conjugation yields and amount of native GCSF. The foregoing data surprisingly show that the amine-polymer with ethylenediamine (Et) as a spacer, for any PEOZ molecular weight, is a poorer substrate when compared to the amine polymer with cadaverine (Cad) or hexylamine (Hex) as the spacer.

Example 14. Determination of Potency of PEOZ-GCSF Conjugates by NFS 60 Cell Proliferation Assay The NFS-60 cell lines are murine myeloblastic cells established from leukemic cells obtained after infection of (NFS X DBA/2) F1 adult mice with Cas Br-M murine leukemia virus. The cells respond to murine interleukin (IL)-3 (IL3), murine or human IL4, human IL6, granulocyte/macrophage colony stimulating factor (GMCSF), GCSF and erythropoietin. The promyelocytic state of NFS-60 cells is maintained in the presence of GCSF. The cells differentiate into neutrophils and macrophages in the presence of IL3 and GMCSF.

These cells were used to measure the in-vitro activity of the PEOZ-GCSF compounds (10 kDa and 20 kDa H-PEOZ-N$^{ter}$-GCSF; and 20 kDa H-PEOZ-GCSF). Sample dilutions of the test articles were made in cell media containing no growth factors. The concentrations prepared were 0.12, 0.024, 0.049, 0.097, 0.195, 0.39, 0.78, 1.56, 3.10, 6.25, 12.5 and 25.0 ng/mL. 96-well plates seeded with NFS 60 cells at a cell density of 2,500 cells/well. The 96-well plates were incubated at 37° C. in an O$_2$/CO$_2$ atmosphere. Test wells received a dilution of the test compounds in cell media (minus growth factors); negative control wells received an equal volume of cell media (minus growth factors); positive controls received an equal amount of GCSF (unconjugated) diluted in an equal volume of cell media (minus growth factors). At 24, 48 and 72 hours cell number was determined using an optical absorbance assay. WST-1 solution was then added to each well, and after a 1-2 hour incubation period the absorbance of each solution was measured at 450 and 620 nm. The amount of formazan dye color produced is a reflection of the viability and number of the cells in each well. The optical density (450-620 nm) is then plotted against GCSF concentration (ng/mL) and compared against the control.

The results of this study are portrayed in FIG. 4 and show the three conjugates of PEOZ-GSCF have similar activity to that of unconjugated GCSF. The EC$_{50}$ activity (using the Hill-Slope method) of GCSF, 10 kDa PEOZ-N$^{ter}$-GCSF, 20 kDa PEOZ-N$^{ter}$-GCSF, 20 kDa PEOZ-hex-GCSF were about 0.06, 0.08, 0.1 and 0.12 ng/mL, respectively.

Example 15. Evaluation the In-Vivo Activity of Polymeric GCSF

Figure 5:
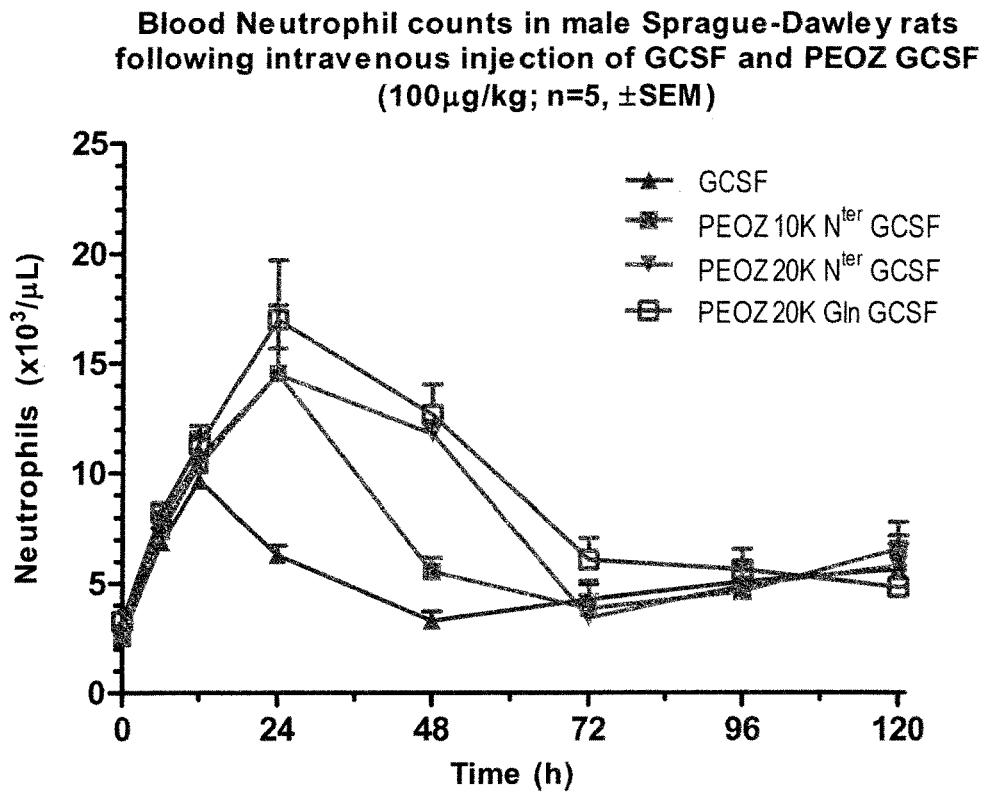
FIG. 5 shows blood neutrophil counts in male Sprague-Dawley rats following intravenous injection of GCSF and 10 kDa PEOZ-N$^{ter}$-GCSF, 20 kDa PEOZ-N$^{ter}$-GCSF, 20 kDa PEOZ-hex-GCSF conjugates.

Sprague-Dawley rats (male, 7-8 weeks old) were used in this study with 5 animals per test article group. The animals were allowed at least 4 days for acclimatization and were allowed food and water ad libitum. The animals were dosed on Day 0, intravenously through the tail vein with either G-CSF, 10 kDa PEOZ-N$^{ter}$-GCSF, 20 kDa PEOZ-N$^{ter}$-GCSF, 20 kDa PEOZ-hex-GCSF. The dose was 100 µg of protein/kg of animal weight. Blood was collected at the following time points: pre-dose, 6, 12, 24, 48, 72, 96, and 120 h post-dose. At each time point, approximately 0.6 mL of blood was removed via a jugular vein catheter with the aid of a syringe. An aliquot of approximately 0.25 mL was placed in tubes containing anticoagulant (K$_2$EDTA) for CBC analysis and stored at 4° C. The remaining blood sample was placed in serum separator tubes and used to harvest serum. Serum was collected, transferred to labeled tubes, and stored at −70° C. FIG. 5 illustrates the blood neutrophil counts in male Sprague-Dawley rats following intravenous injection of GCSF and 10 kDa PEOZ-N$^{ter}$-GCSF, 20 kDa PEOZ-N$^{ter}$-GCSF, 20 kDa PEOZ-hex-GCSF (100 µg/kg; n=5, ±SEM).

Example 16. Conjugation of 5 kDa POZ-Ethylenediamine to hGH Catalyzed by TGAse A solution containing human growth hormone (hGH; 1.5 mg/mL) in 10 mM phosphate buffer pH 7.0 and POZ-NH$_2$ (5 kDa) at 10 fold molar excess with respect to the protein, was prepared. After complete dissolution of the polymer and the protein, TGAse was added at an enzyme to substrate (E/S) ratio of 1:75 by weight and the reaction mixture was incubated at room temperature for 4 h. The reaction mixture was analyzed on a Zorbax GF-250 column (4.6×250 mm) eluting at a flow rate of 0.3 mL/min using 0.2 M phosphate buffer pH 7+20% acetonitrile. The eluent from the column was monitored by measuring the absorbance at 280 nm. Gel filtration chromatography and SDS-page electrophoresis showed the presence of a mono- and a di-conjugate of hGH; approximately 20% of the native hGH was still present resulting in a conjugation efficiency of 80%.

Figure 6:
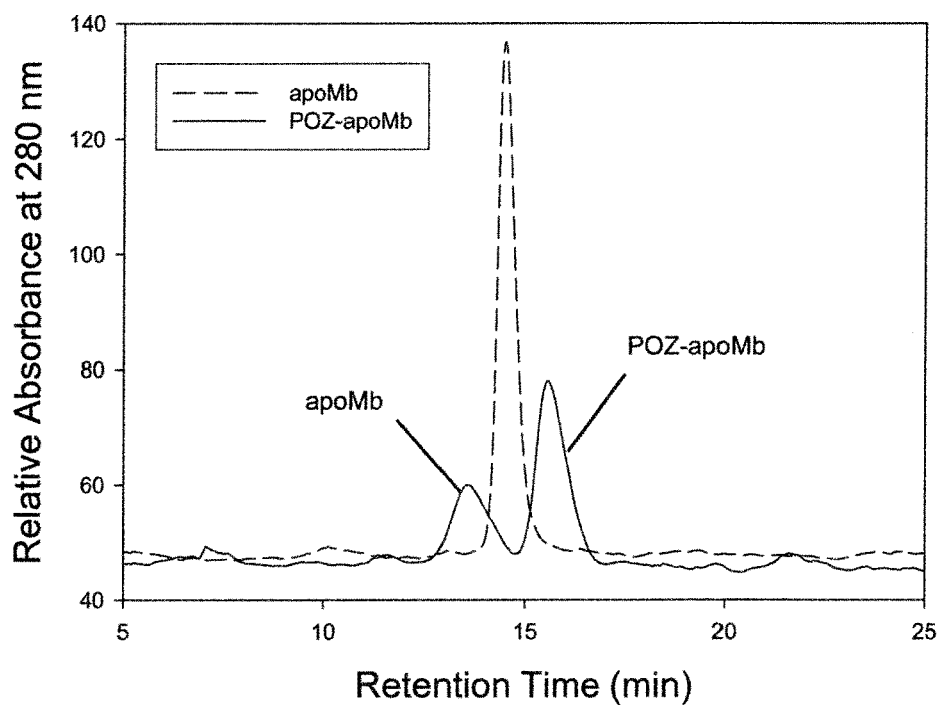
FIG. 6 shows the formation of a 5 kDa POZ-ethylenediamine-apoMB conjugate.

Example 17. Conjugation of 5 kDa POZ-Ethylenediamine to Apomyoglobin (apoMb) Catalyzed by TGAse A solution containing apoMb (0.7 mg/mL) in 10 mM phosphate buffer pH 7.0 and POZ-NH$_2$ (5 kDa) at 100 fold molar excess with respect to the protein, was prepared. After complete dissolution of the polymer and the protein, TGAse was added at an enzyme to substrate (E/S) ratio of 1:75 by weight and the reaction mixture was incubated at room temperature for 4 h. The reaction mixture was analyzed on a Zorbax C18 column (4.6×250 mm) flushing at a flow rate of 1 mL/min. The eluent from the column was monitored by measuring the absorbance at 280 nm. The separation was achieved by a linear gradient of 40-70% acetonitrile containing 0.05% TFA over a 25 min period, followed by an isocratic wash at 80% acetonitrile containing 0.05% TFA. The product was retained and the results are shown in FIG. 6.

Example 18. Conjugation of 30 kDa PEOZ-NHS to Erythropoietin (EPO)

A 10 mL solution of 1.326 mg/mL EPO solution (13.26 mg, 1.0 equiv.) was prepared; the pH of the solution was adjusted to 8.0 by 0.1 N NaOH. To the EPO solution a 1084 µL aliquot of 25 mg/mL H-PEOZ-T-SPA (30 kDa; MW 33,293 Da, 27.1 mg, 1.5 equiv.) in 2 mM HCl was added. The solution was allowed to stir gently at room temperature, while its pH was maintained at 7.9-8.2 by 0.1 N NaOH. Following 45 min of reaction, the reaction was acidified to pH 3.0 with 0.5 M citric acid. Using an AKTA Purifier system (GE Healthcare/Amersham Biosciences), the acidified mixture was loaded onto a 10 mL SP Sepharose HP column (two 5 mL columns connected in series) pre-equilibrated with 20 mM sodium citrate buffer at pH 3.0. Bound proteins were step eluted with 20 mM sodium citrate buffer at pH 3.0 containing 1 M NaCl. Fractions that contain mono-H-PEOZ-EPO were pooled, neutralized to pH 6.9 by 0.1 N NaOH, concentrated, and buffer exchanged into a pH 6.9 formation buffer, which contains phosphate, citrate, sodium chloride, by ultrafiltration in an Amicon™ Stirred Ultrafiltration Cell (Millipore, Model 8050, 50 mL) using a regenerated cellulose membrane (Millipore, YM10, Dia. 44.5 mm, NMWL 10,000). The final conjugate was analyzed by SEC-HPLC with a Shodex Protein KW-803 column monitored at 280 nm using formulation buffer as mobile phase; results were confirmed by SDS-PAGE (data not shown). MALDI-TOF analysis of the purified final product shows the Mn of the conjugate was 59,850.4 Da.

A PEOZ-EPO conjugate with 40 kDa H-PEOZ-T-SPA was also made with the same procedure as described above.

Example 19. Identification of Sites of Polymer Conjugation

Peptide mapping of digested native EPO and PEOZ conjugated EPO was conducted to determine which amino acid residues were modified after conjugation with PEOZ-NHS. In the procedure, mono PEOZ-EPO (30 kDa and 40 kDa) and unconjugated EPO were digested with Endoprotease Lys C, and then mapped on a reverse phase C-18 chromatography column to identify the modified versus unmodified peptide segments as described below.

a. Denaturation and Reduction:

Aliquots of mono PEOZ-EPO solution (347 µg/mL) and unconjugated EPO solution (1.326 mg/mL) were first denatured in a solution containing guanidine HCl (6 M) and EDTA (6 mM) in a pH 8.0 300 mM NaPO$_4$ buffer containing DTT (1.5 µmol). Each aliquot solution contained 100 µg of EPO content. These solutions were gently mixed overnight at room temperature.

b. Carboxymethylation:

Monoiodoacetic acid (1.2 mg of 3.15 µmol) was added to each solution and the vials were covered with aluminum foil, to avoid light exposure, and the mixed room temperature for 45 minutes. The solutions were injected into dialysis cartridges (NMW 2000) and dialyzed against 50 mM Tris HCl buffer (pH8.5)

c. Digestion:

The EPO solution was removed from the dialysis cartridge and placed in reaction tubes. Endoprotease Lys-C enzyme (10 µg) was dissolved in 300 mM NaPO$_4$ solution (100 µL). 20 µL of this Lys-C solution was added to the EPO solution and allowed to digest overnight at 37° C. The next day, the digestion was quenched with 10% TFA solution ($1/10^{th}$ the volume of the digestion solution).

d. Peptide Mapping:

Each of the quenched digested solution was analyzed on a C-18 reverse phase column (Jupiter 5u 300 A 250 mm×4.6 mm) using gradient flow of 0.1% TFA in H$_2$O and 0.1% TFA in ACN mobile phase with a flow rate of 1.0 mL/min. The analytes were detected at a wavelength of 220 nM.

Figure 7:
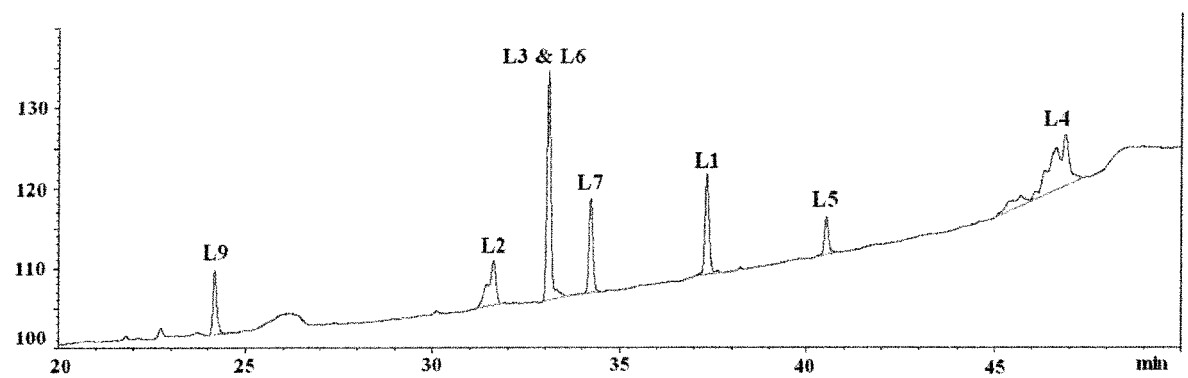
FIG. 7 shows a chromatograms of the peptide maps of Endoprotease Lys C digested EPO.
Figure 8:
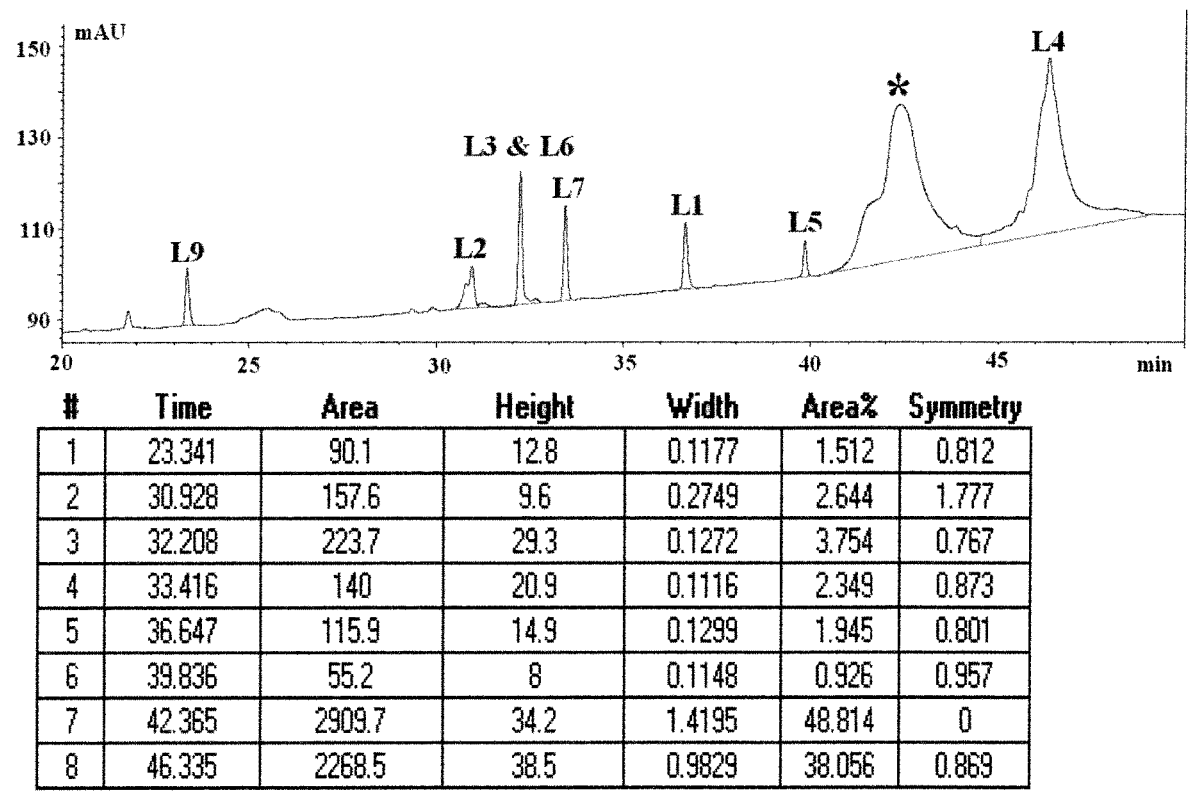
FIG. 8 shows a chromatograms of the peptide maps of Endoprotease Lys C digested PEOZ-EPO conjugate.

FIGS. 7 and 8 are chromatograms of the peptide maps of Endoprotease Lys C digested EPO and PEOZ-EPO, respectively. The digestion of EPO yields 9 peptide fragments, of which 8 fragments are easily chromatographically separated: L1 (AA 1-20), L2 (AA 21-45), L3 (AA 46-52), L4 (AA 53-97), L5 (AA 98-116), L6 (AA 117-140), L7 (AA 141-152) and L9 (AA 155-165). L8 (AA 153-154) has two amino acids and was not retained on the chromatography column. The pattern of digested EPO is similar to that referenced in previous publications. In the chromatograms for the conjugated PEOZ-EPO samples, the L3 & L6 peaks decrease significantly in relation to the L7 peak suggesting that conjugation primarily occurs in the L3 segment at Lysine 52. In addition, the L1 peak also reduces in relation to L7. This suggests that PEOZ is primarily conjugated at Lysine 52 and secondarily to Alanine 1. A new broad peak is detected between the L5 and L4 peaks which correspond to a monoconjugated PEOZ 30 kDa peptide fragment of the L3-L4 segment and the LI segment. Note that PEOZ has an absorbance at 220 nm unlike other polymers such as PEG.

Example 20. Determination of Potency of PEOZ-EPO Conjugates by UT-7 Cell Proliferation Study The UT-7 human leukemia cell line is used to measure EPO dependent cell proliferation activity. UT-7 cells were used to measure the in-vitro activity of the PEOZ-EPO onjugates (30 K and 40 K H-PEOZ-EPO). Dilutions of the test articles and control were made in cell media. The concentrations prepared were 0.125 to 2500 ng/mL. 96 well plates were seeded at a cell density of $4 \times 10^5$ cells per mL. The 96-well plates were incubated at 37° C. in an $O_2/CO_2$ atmosphere for 4 days. Test wells received a dilution of the test compounds in cell media (minus growth factors); negative control wells received an equal volume of cell media (minus growth factors); positive controls received an equal amount of EPO (unconjugated) diluted in an equal volume of cell media (minus growth factors). At 24, 48 and 72 hours cell number was determined using an optical absorbance assay. WST-1 solution was then added to each well, and after a 1-2 hour incubation period the absorbance of each solution was measured at 450 and 620 nm. The amount of formazan dye color produced is a reflection of the viability and number of the cells in each well. The optical density (450-620 nm) is then plotted against EPO concentration (ng/mL) and compared against the control.

Figure 9:
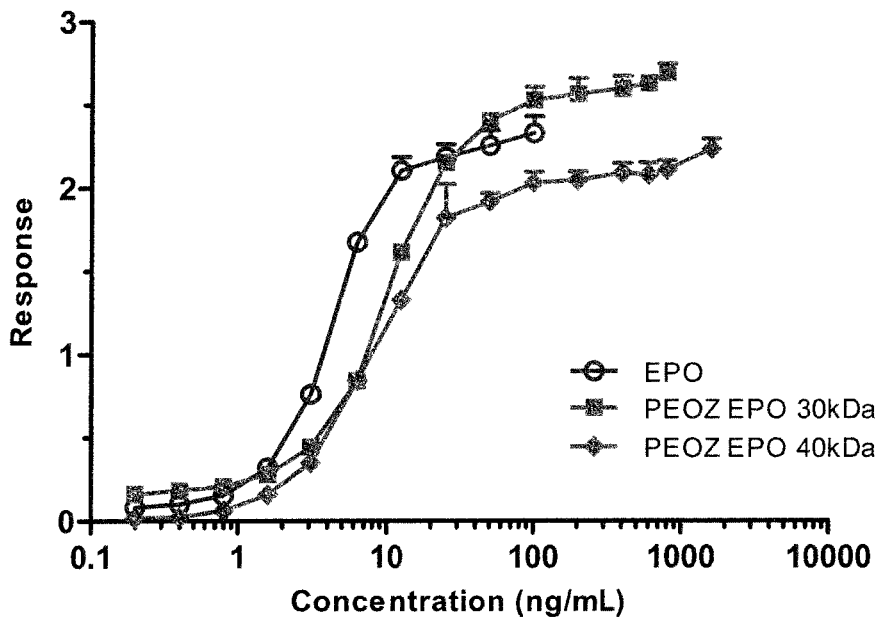
FIG. 9 shows the effect of PEOZ-EPO conjugates by UT-7 cell proliferation.

The results of this study are portrayed in FIG. 9 and they show that two conjugates of PEOZ-EPO (30 kDa and 40 kDa) have similar activity to that of unconjugated EPO. The $EC_{50}$ of native EPO, H-PEOZ-EPO 30 kDa and H-PEOZ-EPO 40 kDa was 4.23 ng/mL, 10.9 ng/mL and 8.8 ng/mL, respectively.

Example 21. In-Vivo Pharmacokinetics and Pharmacodynamics 15 male Sprague-Dawley Rats, 7-8 weeks old, were used in this study. The animals were allowed at least 4 days for acclimatization and were allowed food and water ad libitum. The 15 animals were divided into three groups of 5 animals each. Each group of animals was dosed at Day 0 intravenously (through tail vein) with one dose of either EPO or PEOZ-EPO (30 kDa); control animals received a sham injection. The dose was 25 µg of protein/kg of animal weight. Blood samples were taken at the following time points: pre-dose on day 0 and post-dose at days 1, 3, 7, 11, and 15.

The sample was divided into 2 aliquots. One aliquot was used to measure for reticulocyte counts, hemoglobin levels, RBC, platelets, using microcell counter. The second aliquot was used to prepare serum for bioanalytical measurements. Serum was collected into tubes containing $K_2$ EDTA as the anticoagulant. The bioassay employs the quantitative sandwich enzyme immunoassay technique. A pre-coated plate specific for human EPO was blocked for at least one hour and washed. Standards and samples were pipetted into the wells and any human EPO present was bound by the immobilized antibody. After washing away any unbound substances, a sulfo-tag linked antibody was added to the wells. Following a wash to remove any unbound antibody detection reagent, 1× read buffer was added to the wells and the plate is read immediately by electrochemiluminescence detection (ECL) which emits light in proportion to the concentration. The assay ranges for EPO and PEOZ-EPO were 96 to 70,000 pg/mL and 576 to 420,000 pg/mL, respectively.

Figure 10:
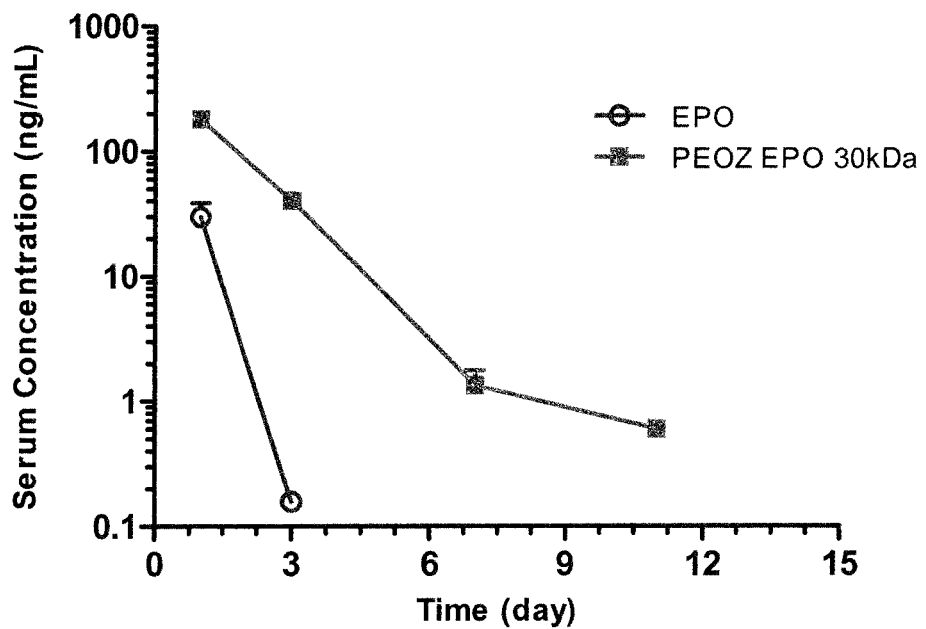
FIG. 10 shows the concentrations of EPO and a PEOZ-EPO conjugate in rat serum.

FIG. 10 is a pharmacokinetic profile that shows the concentrations of EPO and a PEOZ-EPO conjugate in rat serum over a period of 15 days. The data shows PEOZ extends the residence of EPO in rat by a factor of ten times.

Figure 11:
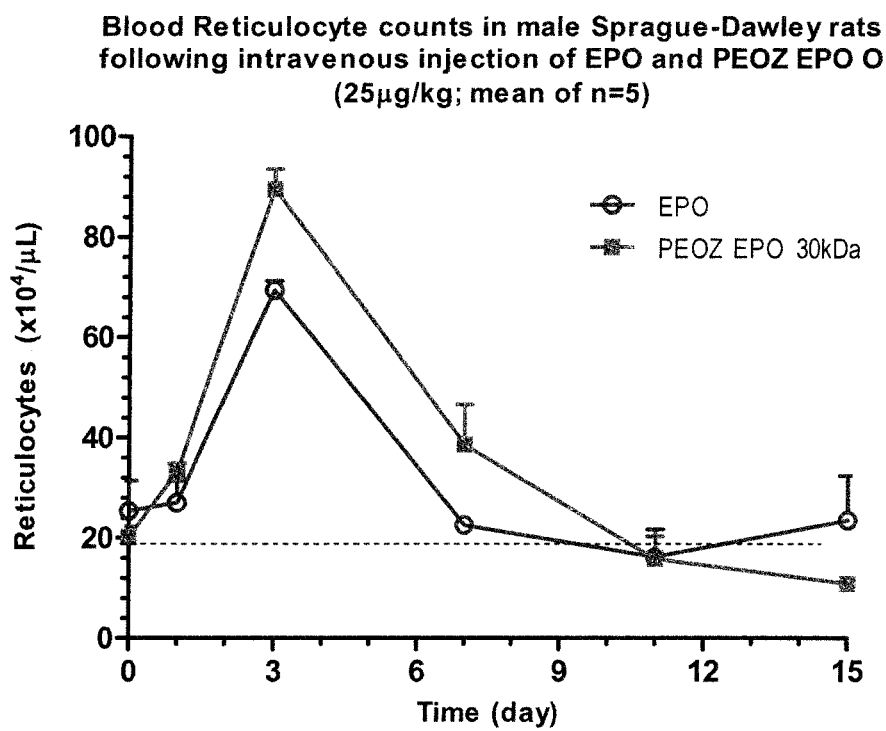
FIG. 11 shows the effect of EPO and PEOZ-EPO conjugates on the reticulocyte counts in rat blood.

FIG. 11 is a pharmacodynamic profile that shows the effect of EPO and PEOZ-EPO conjugates on the reticulocyte counts in rat blood over a period of 15 days. The data shows that reticulocyte counts are increased by a factor of 1.5 times even at day 7.

The foregoing description illustrates and describes certain embodiments of the compounds and applications of the present disclosure. Additionally, the disclosure shows and describes only the exemplary embodiments of the compounds and applications, but as mentioned above, it is to be understood that the teachings of the present disclosure are capable of use in various other combinations, modifications, and environments and is capable of changes or modifications within the scope of the concepts as expressed herein, commensurate with the above teachings and/or the skill or knowledge of the relevant art. The embodiments described hereinabove are further intended to explain best modes known of practicing the invention and to enable others skilled in the art to utilize the invention in such, or other, embodiments and with the various modifications required by the particular applications or uses of the invention. Accordingly, the description is not intended to limit the invention to the form disclosed herein. All references cited herein are incorporated by reference as if fully set forth in this disclosure.

What is claimed:

1. A terminally activated polyoxazoline (POZ) compound of the general structure $R_1$-POZ-$P_p$-$Q_q$-$W_w$-$U_u$-X, wherein POZ is $[N(COR_7)CH_2CH_2]_n$ X is an active functional group;

P is —O—;

q is 0;

p, u and w are each 1;

U is a linking group selected from the group consisting of: —($R_{16}$)$_o$—, —($CR_5R_6$)$_o$—, —NH—$R_{21}$—NHCO—$R_{22}$—;

W is —NH—CO;

$R_7$ is independently selected for each repeating unit of POZ from an unsubstituted or substituted alkyl, alkenyl or aralkyl group;

$R_1$, $R_5$-$R_6$ and $R_{21}$-$R_{22}$ are each independently selected from hydrogen, unsubstituted or substituted alkyl, alkenyl or aralkyl group;

$R_{16}$ is an unsubstituted alkyl, alkenyl or aralkyl group;

n is an integer from 3 to 1000; and o is an integer from 1 to 10.

2. The terminally activated POZ compound of claim 1, wherein the active functional group is protected.

3. The terminally activated POZ compound of claim 1, wherein $R_7$ is an unsubstituted or substituted alkyl, alkenyl having from 1 to 12 carbon atoms.

4. The terminally activated POZ compound of claim 1, wherein $R_7$ is methyl, ethyl or n-propyl.

5. The terminally activated POZ compound of claim 1, wherein the active functional group is selected from the group consisting of: aldehyde, active carbonate (O—CO—Z), maleimide, sulfonate ester (OSO$_2$—$R_{23}$), hydrazide, epoxide, iodoacetamide, alkyne, azide, isocyanate, cyanate isothiocyanate, thiocyanate, nitrile, a carbonyldiimidazole derivative, vinylsulfone, carboxylic acid halide, active ester (—CO—Z) and carboxylic acid, wherein any of the foregoing may be substituted or unsubstituted, Z is an activating group and $R_{23}$ is an unsubstituted or substituted alkyl, alkenyl, alkynyl, aralkyl or aryl group.

6. The terminally activated POZ compound of claim 5, wherein the sulfonate ester is tresylate or mesylate.

7. The terminally activated POZ compound of claim 5, wherein Z is N-succinimidyloxy, chlorine, bromine, sulfo-N-succinimidyloxy, p-nitrophenoxy, 1-imidazolyl, or 1-benzotriazolyloxy.

8. The terminally activated POZ compound of claim 5, wherein the active functional group is a substituted or unsubstituted piperazinyl or a substituted piperidinyl group.

9. The terminally activated POZ compound of claim 1, wherein the POZ polymer has a polydispersity value of less than or equal to 1.05.

10. The terminally activated POZ of claim 1 linked to a target molecule.

11. The terminally activated POZ compound of claim 1, wherein the active functional group forms a linkage with a target molecule and wherein all linkages between the target molecule and the POZ compound are hydrolytically stable in a biological system.

12. A compound having a structure:

(a) $CH_3$—$[N(COCH_2CH_3)CH_2CH_2]_n$—OCONH—$CH_2CH_2$—$NH_2$; or (b) $CH_3$—$[N(COCH_2CH_3)CH_2CH_2]_n$—OCONH—$CH_2$—CHO wherein, n is an integer from 3 to 1000.

* * * * *

SEQUENCE LISTING

<160> NUMBER OF SEQ ID NOS: 1

<210> SEQ ID NO 1
<211> LENGTH: 165
<212> TYPE: PRT
<213> ORGANISM: Homo sapiens

<400> SEQUENCE: 1

```
Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60
```

-continued

```
Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
                100                 105                 110

Gly Ala Gln Lys Glu Ala Ile Ser Pro Pro Asp Ala Ala Ser Ala Ala
            115                 120                 125

Pro Leu Arg Thr Ile Thr Ala Asp Thr Phe Arg Lys Leu Phe Arg Val
    130                 135                 140

Tyr Ser Asn Phe Leu Arg Gly Lys Leu Lys Leu Tyr Thr Gly Glu Ala
145                 150                 155                 160

Cys Arg Thr Gly Asp
                165
```